(12) United States Patent
Yang et al.

(10) Patent No.: US 9,244,074 B2
(45) Date of Patent: Jan. 26, 2016

(54) BIOMARKER OF ASBESTOS EXPOSURE AND MESOTHELIOMA

(75) Inventors: Haining Yang, Honolulu, HI (US); Michele Carbone, Honolulu, HI (US); Harvey I. Pass, New York, NY (US)

(73) Assignees: University of Hawaii, Honolulu, HI (US); New York University, New York, NY (US)

(*) Notice: Subject to any disclaimer, the term of this patent is extended or adjusted under 35 U.S.C. 154(b) by 0 days.

(21) Appl. No.: 14/123,722

(22) PCT Filed: Jun. 7, 2012

(86) PCT No.: PCT/US2012/041428
§ 371 (c)(1),
(2), (4) Date: Dec. 3, 2013

(87) PCT Pub. No.: WO2012/170740
PCT Pub. Date: Dec. 13, 2012

(65) Prior Publication Data
US 2014/0170685 A1    Jun. 19, 2014

Related U.S. Application Data

(60) Provisional application No. 61/494,340, filed on Jun. 7, 2011, provisional application No. 61/502,283, filed on Jun. 28, 2011.

(51) Int. Cl.
G01N 33/53     (2006.01)
G01N 33/574    (2006.01)
G01N 33/68     (2006.01)

(52) U.S. Cl.
CPC .... G01N 33/57423 (2013.01); G01N 33/57484 (2013.01); G01N 33/6875 (2013.01)

(58) Field of Classification Search
None
See application file for complete search history.

(56) References Cited

U.S. PATENT DOCUMENTS

| | | | |
|---|---|---|---|
| 4,444,887 A | 4/1984 | Hoffmann |
| 4,474,893 A | 10/1984 | Reading |
| 4,612,132 A | 9/1986 | Wollenberg et al. |
| 4,676,980 A | 6/1987 | Segal et al. |
| 4,714,681 A | 12/1987 | Reading |
| 4,716,111 A | 12/1987 | Osband et al. |
| 4,741,900 A | 5/1988 | Alvarez et al. |
| 4,816,397 A | 3/1989 | Boss et al. |
| 4,816,567 A | 3/1989 | Cabilly et al. |
| 4,908,773 A | 3/1990 | Pantoliano et al. |

(Continued)

FOREIGN PATENT DOCUMENTS

| | | |
|---|---|---|
| EP | 0 239 400 | 9/1987 |
| EP | 0 367 166 | 5/1990 |

(Continued)

OTHER PUBLICATIONS

Liu et al. (Am. J. Respir Cell Mol. Biol. 2010 vol. 43, p. 530-538.*

(Continued)

*Primary Examiner* — Jacob Cheu
(74) *Attorney, Agent, or Firm* — Knobbe, Martens, Olson & Bear, LLP

(57) ABSTRACT

Several embodiments provided herein relate to methods of diagnosing asbestos exposure or mesothelioma. Several embodiments also relate to methods of differentiating whether a tumor of the lung is lung cancer or mesothelioma.

11 Claims, 7 Drawing Sheets

(56) References Cited

U.S. PATENT DOCUMENTS

| | | | |
|---|---|---|---|
| 4,925,648 A | 5/1990 | Hansen et al. |
| 4,946,778 A | 8/1990 | Ladner et al. |
| 5,010,175 A | 4/1991 | Rutter et al. |
| 5,112,946 A | 5/1992 | Maione |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,288,514 A | 2/1994 | Ellman |
| 5,314,995 A | 5/1994 | Fell, Jr. et al. |
| 5,331,573 A | 7/1994 | Balaji et al. |
| 5,336,603 A | 8/1994 | Capon et al. |
| 5,349,053 A | 9/1994 | Landolfi |
| 5,359,046 A | 10/1994 | Capon et al. |
| 5,359,115 A | 10/1994 | Campbell et al. |
| 5,403,484 A | 4/1995 | Ladner et al. |
| 5,413,923 A | 5/1995 | Kucherlapati et al. |
| 5,420,328 A | 5/1995 | Campbell |
| 5,427,908 A | 6/1995 | Dower et al. |
| 5,436,850 A | 7/1995 | Eisenberg et al. |
| 5,447,851 A | 9/1995 | Beutler et al. |
| 5,474,981 A | 12/1995 | Leder et al. |
| 5,506,337 A | 4/1996 | Summerton et al. |
| 5,516,637 A | 5/1996 | Huang et al. |
| 5,519,134 A | 5/1996 | Acevedo et al. |
| 5,525,735 A | 6/1996 | Gallop et al. |
| 5,530,101 A | 6/1996 | Queen et al. |
| 5,539,083 A | 7/1996 | Cook et al. |
| 5,545,806 A | 8/1996 | Lonberg et al. |
| 5,549,974 A | 8/1996 | Holmes |
| 5,557,535 A | 9/1996 | Srinivasan et al. |
| 5,565,332 A | 10/1996 | Hoogenboom et al. |
| 5,569,588 A | 10/1996 | Ashby et al. |
| 5,569,825 A | 10/1996 | Lonberg et al. |
| 5,571,698 A | 11/1996 | Ladner et al. |
| 5,573,920 A | 11/1996 | Randle |
| 5,580,717 A | 12/1996 | Dower et al. |
| 5,585,089 A | 12/1996 | Queen et al. |
| 5,593,853 A | 1/1997 | Chen et al. |
| 5,595,756 A | 1/1997 | Bally et al. |
| 5,601,819 A | 2/1997 | Wong et al. |
| 5,605,793 A | 2/1997 | Stemmer |
| 5,622,929 A | 4/1997 | Willner et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,658,727 A | 8/1997 | Barbas et al. |
| 5,658,759 A | 8/1997 | Bebbington |
| 5,661,016 A | 8/1997 | Lonberg et al. |
| 5,677,425 A | 10/1997 | Bodmer et al. |
| 5,698,426 A | 12/1997 | Huse |
| 5,714,350 A | 2/1998 | Co et al. |
| 5,733,743 A | 3/1998 | Johnson et al. |
| 5,750,753 A | 5/1998 | Kimae et al. |
| 5,780,225 A | 7/1998 | Wigler et al. |
| 5,789,208 A | 8/1998 | Sharon |
| 5,807,715 A | 9/1998 | Morrison et al. |
| 5,811,238 A | 9/1998 | Stemmer et al. |
| 5,814,318 A | 9/1998 | Lonberg et al. |
| 5,821,047 A | 10/1998 | Garrard et al. |
| 5,827,739 A | 10/1998 | Wilson et al. |
| 5,830,721 A | 11/1998 | Stemmer et al. |
| 5,834,252 A | 11/1998 | Stemmer et al. |
| 5,837,458 A | 11/1998 | Minshull et al. |
| 5,869,046 A | 2/1999 | Presta et al. |
| 5,873,052 A | 2/1999 | Sharaf |
| 5,879,936 A | 3/1999 | Bebbington et al. |
| 5,880,972 A | 3/1999 | Horlbeck |
| 5,884,230 A | 3/1999 | Srinivasan et al. |
| 5,885,573 A | 3/1999 | Bluestone et al. |
| 5,885,779 A | 3/1999 | Sadowski et al. |
| 5,885,793 A | 3/1999 | Griffiths et al. |
| 5,888,738 A | 3/1999 | Hendry |
| 5,916,771 A | 6/1999 | Hori et al. |
| 5,939,598 A | 8/1999 | Kucherlapati et al. |
| 5,969,108 A | 10/1999 | McCafferty et al. |
| 5,981,216 A | 11/1999 | Kenten et al. |
| 6,087,186 A | 7/2000 | Cargill et al. |
| 6,121,022 A | 9/2000 | Presta et al. |
| 6,165,745 A | 12/2000 | Ward et al. |
| 6,184,223 B1 | 2/2001 | Kahn et al. |
| 6,194,551 B1 | 2/2001 | Idusogie et al. |
| 6,277,375 B1 | 8/2001 | Ward |
| 6,335,163 B1 | 1/2002 | Sharon |
| 6,350,861 B1 | 2/2002 | Co et al. |
| 6,448,223 B1 | 9/2002 | Tracey et al. |
| 6,465,422 B1 | 10/2002 | Schmidt et al. |
| 6,468,533 B1 | 10/2002 | Tracey et al. |
| 6,555,651 B2 | 4/2003 | Stern et al. |
| 6,737,056 B1 | 5/2004 | Presta |
| 6,821,505 B2 | 11/2004 | Ward |
| 7,485,697 B2 | 2/2009 | Yamamoto et al. |
| 7,732,400 B2 | 6/2010 | Stern et al. |
| 2003/0060410 A1* | 3/2003 | Tracey et al. ............ 514/12 |
| 2003/0144201 A1 | 7/2003 | Tracey et al. |
| 2003/0190311 A1 | 10/2003 | Dall'Acqua et al. |
| 2004/0002587 A1 | 1/2004 | Watkins et al. |
| 2004/0005316 A1 | 1/2004 | Tracey et al. |
| 2004/0110833 A1* | 6/2004 | Fink et al. ............ 514/546 |
| 2004/0136979 A1* | 7/2004 | Bianchi et al. ........... 424/130.1 |
| 2004/0242481 A1 | 12/2004 | Bianchi et al. |
| 2006/0111287 A1 | 5/2006 | Bianchi |
| 2006/0188883 A1 | 8/2006 | Murray et al. |
| 2007/0286858 A1 | 12/2007 | Clancy et al. |
| 2008/0261258 A1 | 10/2008 | Smith et al. |
| 2008/0311122 A1 | 12/2008 | Wu et al. |
| 2009/0003640 A1 | 1/2009 | Burnett |
| 2009/0148453 A1 | 6/2009 | Newman et al. |
| 2009/0221542 A1* | 9/2009 | Wang et al. ............ 514/172 |
| 2010/0061987 A1 | 3/2010 | Wu et al. |
| 2010/0104589 A1 | 4/2010 | Govindan et al. |
| 2010/0129379 A1 | 5/2010 | Carpenter et al. |
| 2010/0143349 A1 | 6/2010 | Hufton et al. |
| 2010/0152239 A1* | 6/2010 | Ulloa et al. ............ 514/318 |
| 2011/0091928 A1* | 4/2011 | Tamai et al. ............ 435/29 |
| 2011/0104174 A1 | 5/2011 | Strakhova et al. |
| 2014/0127134 A1 | 5/2014 | Yang et al. |

FOREIGN PATENT DOCUMENTS

| | | |
|---|---|---|
| EP | 0 396 387 | 11/1990 |
| EP | 0 413 622 | 2/1991 |
| EP | 0 439 095 | 7/1991 |
| EP | 0 519 596 | 12/1992 |
| EP | 0 592 106 | 4/1994 |
| EP | 1 176 195 | 1/2002 |
| WO | WO 84/03564 | 9/1984 |
| WO | WO 86/05807 | 10/1986 |
| WO | WO 88/07089 | 9/1988 |
| WO | WO 89/01036 | 2/1989 |
| WO | WO 89/12624 | 12/1989 |
| WO | WO 90/02809 | 3/1990 |
| WO | WO 91/00360 | 1/1991 |
| WO | WO 91/06570 | 5/1991 |
| WO | WO 91/09967 | 7/1991 |
| WO | WO 91/10737 | 7/1991 |
| WO | WO 91/10741 | 7/1991 |
| WO | WO 91/14438 | 10/1991 |
| WO | WO 91/19735 | 12/1991 |
| WO | WO 92/00091 | 1/1992 |
| WO | WO 92/01047 | 1/1992 |
| WO | WO 92/05793 | 4/1992 |
| WO | WO 92/08495 | 5/1992 |
| WO | WO 92/08802 | 5/1992 |
| WO | WO 92/18619 | 10/1992 |
| WO | WO 92/22324 | 12/1992 |
| WO | WO 93/11236 | 6/1993 |
| WO | WO 93/15199 | 8/1993 |
| WO | WO 93/15200 | 8/1993 |
| WO | WO 93/17715 | 9/1993 |
| WO | WO 93/20242 | 10/1993 |
| WO | WO 93/21232 | 10/1993 |
| WO | WO 93/25788 | 12/1993 |

(56) References Cited

FOREIGN PATENT DOCUMENTS

| WO | WO 94/02935 | 2/1994 |
|---|---|---|
| WO | WO 95/15982 | 6/1995 |
| WO | WO 95/20401 | 8/1995 |
| WO | WO 96/04388 | 2/1996 |
| WO | WO 96/33735 | 10/1996 |
| WO | WO 96/34096 | 10/1996 |
| WO | WO 97/00271 | 1/1997 |
| WO | WO 97/33899 | 9/1997 |
| WO | WO 97/34631 | 9/1997 |
| WO | WO 97/34911 | 9/1997 |
| WO | WO 98/01879 | 1/1998 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 99/23105 | 5/1999 |
| WO | WO 99/54342 | 10/1999 |
| WO | WO 99/58572 | 11/1999 |
| WO | WO 00/42072 | 7/2000 |
| WO | WO 01/77137 | 10/2001 |
| WO | WO 02/060919 | 8/2002 |
| WO | WO 02/074337 | 9/2002 |
| WO | WO 03/035835 | 5/2003 |
| WO | WO 03/075957 | 9/2003 |
| WO | WO 2004/009618 | 1/2004 |
| WO | WO 2004/029207 | 4/2004 |
| WO | WO 2006/024547 | 3/2006 |
| WO | WO 2011/030334 | 3/2011 |
| WO | WO 2012/170740 | 12/2012 |
| WO | WO 2012/170742 | 12/2012 |

OTHER PUBLICATIONS

Yang et al. (PNAS 2010 vol. 107, p. 12611-12616.*
Chung et al. J. Translational Medicine 2009, vol. 7, p. 38-48.*
Naumnik et al. Folia Histochem. Cytobiol. 2009 vol. 47, p. 703-709.*
U.S. Appl. No. 08/081,577, filed Jun. 21, 1993, Campbell et al.
Alegre et al., 'A Non-Activating Humanized Anti-CD3 Monoclonal Antibody Retains Immunosuppressive Properties In Vivo', 1994, Transplantation 57:1537-1543.
Allen, F. H., et al., 'The Cambridge Crystallographic Data Centre: Computer-Based Search, Retrieval, Analysis and Display of Information', *Acta Crystallogr.*, B35: 2331-2339 (1979).
Arnon et al., 'Monoclonal Antibodies for Immunotargeting of Drugs in Cancer Therapy', in Monoclonal Antibodies and Cancer Therapy, Reisfeld et al. (eds.), pp. 243-256 (Alan R. Liss, Inc. 1985).
Armour et al., 'Recombinant human IgG molecules lacking Fcy receptor I binding and monocyte triggering activites', 1999, Eur J Immunol 29:2613-2624.
Armstrong et al., 'A Pahse I Study of Chemically Synthesized Verotoxin (Shiga-like Toxin) Pk-Trisaccharide Receptors Attached to Chromosorb for Preventing Hemolytic-Uremic Syndrome', J. Infectious Diseases 171:1042-1045 (1995).
Ashkenazi et al., 'Protection against endotoxic shock by a tumor necrosis factor receptor immunoadhesin', 1991, Proc. Natl. Acad. Sci. USA 88: 10535-10539.
Auerbach et al., 'Angiogenesis assays: Problems and pitfalls', (Cancer and Metastasis Reviews, 2000, 19: 167-172).
Ausubel et al., 'Short Protocols in Molecular Biology', (eds.), Current Protocols in Molecular Biology, John Wiley & Sons, NY (1995).
Baldwin et al. (eds.), "Analysis, Results, and Future Prospective of the Therapeutic Use of Radiolabeled Antibody in Cancer Therapy", in Monoclonal Antibodies for Cancer Detection and Therapy, pp. 303-316 (Academic Press 1985).
Bao, J., 'Capillary electrophoretic immunoassays', Chromatogr. B. Biomed. Sci. 699:463-80 (1997).
Baum, 'Solid-phase synthesis of benzodiazepines', C&EN, benzodiazepines, Jan. 18, 1993, p. 33.
Bebbington et al., The use of vectors based on gene amplification for the expression of cloned genes in mammalian cells in DNA cloning, vol. 3. (Academic Press, New York, 1987).

Bertino et al, 'Matinib mesylate enhances therapeutic effects of gemcitabine in human malignant mesothelioma xenografts', Clin Cancer Res. 2008;14(2):541-548.
Better et al., '*Escherichia coli* Secretion of an Active Chimeric Antibody Fragment', *Science* 240:1041-1043 (1988).
Bianchi, 'DAMPs, PAMPs and alarmins: all we need to know about danger', ME (2007), J Leukoc Biol 81: 1-5; 13-15.
Bitter et al., 'Vectors for Expression of Cloned Genes', *Methods in Enzymol.* 153:51-544 (1987).
BLAST and Gapped BLAST programs, the default parameters of the respective programs (e.g., BLASTN). See http://www.ncbi.nlm.nih.gov, as available on Apr. 10, 2002.
Bocchetta M, et al., "Human mesothelial cells are unusually susceptible to simian virus 40-mediated transformation and asbestos cocarcinogenicity," Proc Natl Acad Sci USA. 2000; 97:10214-10219.
Bonovas, "*Cancer Chemoprevention: A Summary of the Current Evidence*", et al (Anticancer Research. 28: 1857-1866 (2008)).
Bork, "Powers and Pitfalls in Sequence Analysis", (Genome Research, 2000, 10:398-400).
Bowie et al., 'Deciphering the Message in Protein Sequences: Tolerance to Amino Acid Substitutions', (Science, 1990, 247:1306-1310).
Brown et al., "*Tolerance to Single, but Not Multiple, Amino Acid Replacements in Antibody Vh CDR2*", (J Immunol. May 1996;156(9):3285-91 at 3290 and Tables 1 and 2).
Burgess et al., 'Possible Dissociation of the Heparin-binding and Mitogenic Activites of Heparin-binding (Acidic Fibroblast) Growth Factor-1 from Its Receptor-binding Activites by Site-directed Mutagenesis of a Single Lysine Residue', (J. Cell Biol. 111:2129-2138, 1990).
Campbell et al., 'Phosphonate Ester Synthesis Using a Modified Mitsunobu Condensation', 1994, J. Org. Chem., 59:658.
Carbone M. et al., (2006) 'The pathogenesis of mesothelioma', (Translated from eng) Semin Diagn Pathol 23(1):56-60 (in eng).
Carrell et al., 'New promise in combinatorial chemistry: synthesis, characterization, and screening of small-molecule libraries in solution', Chem Biol. 2:171-183, 1995.
Chen et al., '"Analogous" Organic Synthesis of Small-Compound Libraries: Validation of Combinatorial Chemistry in Small-Molecule Synthesis', 1994, J. Amer. Chem. Soc., 116:2661.
Chien et al., 'The two-hybrid system: A method to identify and clone genes for proteins that interact with a protein of interest', Proc. Natl. Acad. Sci. USA 88:9578-9582 (1991).
Cho, et al., 'An Unnatural Biopolymer', 1993 Science 261:1303-1305.
Choe N, et al., 'Pleural Macrophage Recruitment and Activation in Asbestos in Asbestos-induced Pleural Injury', (1997) Pleural macrophage recruitment and activation in asbestos-induced pleural injury. (Translated from eng) Environ Health Perspect 105 Suppl 5:1257-1260 (in eng).
Clackson et al., 'Making antibody fragments using phage display libraries', *Nature* 352: 624-628, 1991.
Clark et al., 'Discovery and Development of Janus Kinase (JAK) Inhibitors for Inflammatory Diseases', (J. Med. Chem., 2014, 57(12), pp. 5023-5038).
Cockett et al., 'High Level Expression of Tissue Inhibitor of Metalloproteinases in Chinese Hamster Ovary Cells Using Glutamine Synthetase Gene Amplification', *Bio/Technology* 8:2 (1990).
Colberre-Garapin et al., 'A New Dominant Hybrid Selective Marker for Higher Eukaryotic Cells', *J. Mol. Biol.* 150:1 (1981).
Crouse et al., 'Expression and amplification of engineered mouse dihydrofolate reductase minigenes', *Mol. Cell. Biol.* 3:257 (1983).
Denardo et al., 'Comparison of 1,4,7,10-tetraazacylododecane-N, N', N",N"'-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts', 1998, Clin Cancer Res 4:2483.
Dracopoli et al., 'Vectors for Gene Therapy', (eds), Current Protocols in Human Genetics, John Wiley & Sons, NY (1994), Chapter 12.
Dracopoli et al., 'Delivery Systems for Gene Therapy', (eds), Current Protocols in Human Genetics, John Wiley & Sons, NY (1994), Chapter 13.
Duncan et al, 'Localization of the binding site for the human high-affinity Fc receptor on IgG', 1988, Nature 332:563-564.

(56) References Cited

OTHER PUBLICATIONS

Erickson et al., 'Design, Activity, and 2.8 A Crystal Structure of a C2 Symmetric Inhibitor Complexed to HIV-1 Protease', *Science* 249:527-533 (1990).

Fell et al., 'Genetic construction and characterization of a fusion protein consisting of a chimeric F(ab') with specificity for carcinomas and human IL-2', 1991, J. Immunol. 146:2446-2452.

Fetrow et al., 'Method for Prediction of Protein Function from Sequence using the Sequence-to-Structure-to-Function Paradigm with Application to Glutaredoxins/Thioredoxins and T1 Ribonucleases', *J. Mol. Biol.* 281: 949-968 (1998).

Fetrow et al., 'Functional Analysis of the *Escherichia coli* Genome Using the Sequence-to-Structure-to-Function Paradigm: Identification of Proteins Exhibiting the Glutaredoxin/Thioredoxin in Disulfide Oxidoreductase Activity', *J. Mol. Biol.* 282:703-711 (1998).

Field et al., 'A novel genetic system to detect protein-protein interactions', *Nature* 340:245-246 (1989).

Fink MP, 'Ethyl Pyruvate: A Novel Treatment for Sepsis', Curr Drug Targets. 2007;8(4):515-8.

Foecking et al., 'Powerful and versatile enhancer-promoter unit for mammalian expression vectors', *Gene* 45:101 (1986).

Furka, 'General method for rapid synthesis of multicomponent peptide mixtures', 1991, Int. J. Pept. Prot. Res., 37:487-493.

Garnett, 'Targeted drug conjugates: principles and progress,' 2002, Adv Drug Deliv Rev 53:171.

Gentz et al., 'Bioassay for trans-activation using purified human immunodeficiency virus tat-encoded protein: Trans-activation requires mRNA synthesis', *Proc. Natl. Acad. Sci. USA* 86:821-824 (1989).

Ghetie et al., 'Increasing the serum persistence of an IgG fragment by random mutagenesis', 1997, Nat. Biotech. 15:637-40.

Gillies et al., 'High-level expression of chimeric antibodies using adapted cDNA variable region cassettes', (1989) *J. Immunol. Methods* 125:191-202.

Gillies et al., 'Antibody-targeted interleukin 2 stimulates T-cell killing of autologous tumor cells', 1992, PNAS 89:1428-1432.

Greenspan et al., 'Idiotypes: structure and immunogenicity', *FASEB J.* 7(5):437-444; (1989).

Guido et al., 'Virtual Screening and Its Integration with Modern Drigs Design Technologies', (Curr Med Chem. 2008;15(1):37-46).

Gura T., 'Systems for Identifying New Drugs Are Often Faulty', (Science, 1997, 278(5340): 1041-1042, encloses 1-5).

Hagihara et al., 'Vinylogous Polypeptides: An Alternative Peptide Backbone', 1992, J. Amer. Chem. Soc., 114:6568.

Hammerling, et al., 'Monoclonal Antibodies and T-Cell Hybridomas', 563-681 (Elsevier, N.Y., 1981).

Hansson, et al., 'Evolution of Differential Substrate Specificities in Mu Class Glutathione Transferases Probed by DNA Shuffling', 1999, J. Mol. Biol. 287:265-76.

Harayama, 'Artifical evolution by DNA shuffling', 1998, Trends Biotechnol. 16(2): 76-82.

Harlow et al., 'Antibodies: A Laboratory Manual', (Cold Spring Harbor Laboratory Press, 2nd ed. 1988).

Haugland,'Handbook of Fluorescent Probes and Research Chemicals', (1996).

Hellstrom et al., 'Antibodies for Drug Delivery', in Controlled Drug Delivery (2nd Ed.), Robinson et al. (eds.), pp. 623-653 (Marcel Dekker, Inc. 1987).

Hirschmann et al., 'Nonpeptidal Peptidomimetics with a β-D-Glucose Scaffolding. A Partial Somatostatin Agonist Bearing a Close Structural Relationship to a Potent, Selective Substance P Antagonist', 1992, J. Amer. Chem. Soc., 114:9217-9218.

HMGB1 ELISA Kit Instructions, IBL International, in 9 pages, dated Jan. 7, 2011.

Hobbs et al., '"Diversomers": An approach to nonpeptide, nonoligomeric checmical diversity', 1993, Proc. Natl. Acad. Sci. USA, 90:6909-6913.

Hodgson, 'Data-Directed Drug Design', *Bio. Technology* 9:19-21 (1991).

Houghton et al., 'Generation and use of synthetic peptide combinatorial libraries for basic research and drug discovery', 1991, Nature, 354:84-88.

Hruby, et al., 'Emerging approaches in the molecular design of receptor-selective peptide ligands: conformational, topographical and dynamic considerations', 1990 *Biochem J* 268(2):249-262.

Huston et al., 'Protein Engineering of Single-Chain Fv Analogs and Fusion Proteins', Methods in Enzymology 203:46-88 (1991).

Hutchins et al., 'Improved biodistribution, tumor targeting, and rediced immunogenicity in mice with a y4 variant of Campath-1H', 1995, Proc Natl. Acad Sci USA 92:11980-11984.

Huttunen HJ et al., 'Amphoterin as an extracellular regulator of cell motility: from discovery to disease', *J Intern Med.* 2004;255:351-366.

Idusogie et al, 'Mapping of the C1q Binding Site on Rituxan, a Chimeric Antibody with a human IgG1 Fc', 2000, J Immunol 164:4178-4184.

Idusogie et al, 'Engineered Antibodies with Increased Activity to Recruit Complement', 2001, J Immunol 166:2571-2575.

Inouye & Inouye, 'Up-promoter mutations in the Ipp gene of *Escherichia coli*', Nucleic Acids Res. 13:3101-3109 (1985).

International Search Report and Written Opinion dated Jan. 29, 2013 in Application No. PCT/US2012/041428.

International Search Report and Written Opinion dated Feb. 1, 2013 in Application No. PCT/US2012/041430.

Jain RK, 'Barriers to Drug Delivery in Solid Tumors', (Scientific American, Jul. 1994, 58-65).

Jefferis et al, 'Recognition sites on human IgG for Fcy receptors : the role of glycosylation', 1995, Immunol Lett. 44:111-117.

Jefferis et al, 'Modulation of FcyR and human complement actication by IgG3-core oligosaccharide interactions', 1996, Immunol Lett 54:101-104.

Jefferis et al, 'Interaction sites on human IgG-Fc for FcyR : current models', 2002, Immunol Lett 82:57-65.

Jespers et al., 'Guiding the Selection of Human Antibodies from Phage Display Repertoires to a Single Epitope of an Antigen', *Bio/technology* 12:899-903 (1988).

Jones et al., 'Replacing the complementarity-determining regions in a human antibody with those from a mouse', *Nature* 321:522-525, 1986.

Karlin et al., 'Applications and statistics for multiple high-scoring segments in molecular sequences', Proc. Natl. Acad. Sci. USA, 90:5873-5877 (1993).

Kohler, 'Immunoglobulin chain loss in hybridoma lines', *Proc. Natl. Acad. Sci. USA* 77:2197 (1980).

Kostelny et al., 'Formation of a Bispecific Antibody by the Use of Leucine Zippers', J. Immunol. 148:1547-1553 (1992).

Kriegler, 'Gene Transfer and Expression, A Laboratory Manual', Stockton Press, NY (1990).

Lam K.S., 'Application of combinatorial library methods in cancer research and drug discvoery', *Anticancer Drug Res.*, 12:145-167 (1997).

Lazar et al., 'Transforming Growth Factor α: Mutation of Aspartic Acid 47 and Leucine 48 Results in Different Biological Activities', (Mol. Cell. Biol., 8:1247-1252, 1988).

Leanna et al., 'The reverse two-hybrid system: a genetic scheme for selection against specific protein/protein ineractions', *Nucl. Acid Res.* 24:3341-3347 (1996).

Liang et al., 'Parallel Synthesis and Screening of a sSolid Phase Carbohydrate Library', 1996, Science, 274-1520-1522.

Lipinski et al., 'Experimental and computational approaches to estimate solubility and permeability in drug discovery and development settings', Adv. Drug Delivery Rev. 23:3-25, 1997.

Logan et al., 'Adenovirus tripartite leader sequence enhances translation of mRNAs late after infection', *Proc. Natl. Acad. Sci. USA* 81:355-359 (1984).

Lonberg et al., 'Human Antibodies from Transgenic Mice', *Int. Rev. Immunol.* 13:65-93 (1995).

Lorenzo et al., 'PCR-Based Method for the Introduction of Mutations in Genes Cloned and Expressed in Vaccinia Virus', 1998, Biotechniques 24(2): 308-313.

(56) References Cited

OTHER PUBLICATIONS

Lowman HB, 'Bacteriphage Display and Discovery of Peptide Leads for Drug Development', *Annu. Rev. Biophys. Biomol. Struct.* 26:401-424 (1997).
Lowy et al., 'Isolation of Transforming DNA: Cloning the Hamster aprt Gene', *Cell* 22:817 (1980).
Lund et al., 'Human FcγRI and FcγRII Interact with Distinct but Overlapping Sites on Human IfG1', 1991, J. Immunol. 147:2657-2662.
Lund et al, 'Multiple Binding Sites on the CH2 Domain of IgG for Mouse FcγR11', 1992, Mol Immunol 29:53-59.
Lund et al., 'Oligosaccharide-protein interactions in IgG can modulate recognition by Fcγ receptors' 1995, Faseb J 9:115-119.
Lund et al, 1996, 'Multiple Interactions of IgG with Its Core Oligosaccharide Can Modulate Recognition by Complement and Human Fcγ Receptor I and Influence the SYnthesis of Its Oligosaccharide Chains1', J Immunol 157:4963-4969.
Ma, 'Animal Models of Disease', (Modern Drug Discovery 2004, 7(6).
Marks et al., 'By-Passing Immunization: Building High Affinity Human Antibodies by Chain Shuffling', *Biotechnology* 10:779-783, 1992.
Mathis G., 'Probing Molecular Interactions with Homogeneous Techniques Based on Rare Earth Cryptates and Fluorescence Energy Transfer', *Clin. Chem.* 41:139-147 (1995).
May, 'Trends in Biotechnology', 1993, *TIB TECH* 11(5):155-215.
McCafferty et al., 'Phage antiboides: filamentous phage displaying antibody variable domains', *Nature* 348:552-554, 1990.
Merler et al., 'Surveillance and intervention studies on respiratory cancers in asbestos-exposed workers', (Scand J Work Enviorn Health 1997;23(2):83-92).
Moore, W.J., Physical Chemistry, 4th Edition, Prentice-Hall, N.J. (1972).
Morgan et al., 'Human Gene Therapy', *Ann. Rev. Biochem.* 62:191-217 (1993).
Morgan, et al. 'Chapter 26. Approaches to the Discovery of Non-Peptide Ligands for Peptide Receptors and Peptidases', 1989 *Ann Rep Med Chem* 24:243-252.
Morrison, 'Transfectomas Provide Novel Chimeric Antibodies', *Science* 229:1202 (1985).
Mulligan, 'Selection for animal cells that express the *Escherichia coli* gene coding for xanthine-guanine phosphoribosyltransferase', *Science* 260:926-932 (1993).
Mulligan et al., 'The Basic Science of Gene Therapy', *Proc. Natl. Acad. Sci. USA* 78:2072 (1981).
Mullinax et al., 'Expression of a Heterodimeric Fab Antibody Protein in One Cloning Step', *BioTechniques* 12(6):864-869 (1992).
Murray, et al., 'Burger's Medicinal Chemistry and Drug Discovery', 5th ed., vol. 1, Manfred E. Wolf, ed., John Wiley and Sons, Inc., 1995.
Naramura et al., 'Mechanisms of cellular cytotoxicity mediated by a recombinant antibody-IL2 fusion protein against human melanoma cells', 1994, Immunol. Lett. 39:91-99.
NCBI databse entry for HMGB1 (downloaded Nov. 2, 2014 from http://www.ncbi.nlm.nih.gov/gene?term=(hmgb1[gene])%20AND%20(Homo%20sapiens[orgn})%20AND%20alive[prop]%20NOT%20newentry[gene]&sort=weight).
Neri 'Chemoprevention of Asbestos-linked Cancers: A Systematic Review' (Anticancer Research. 32:1005-1014 (2012).
Nissinoff, J., *'Idiotypes: Concepts and Applications'*, *Immunol.* 147(8):2429-2438 (1991).
O'Hare et al., 'Transformation of mouse fibroblasts to methotrexate resistance by a recombinant plasmid expressing a prokaryotic dihydrofolate reductase', *Proc. Natl. Acad. Sci. USA* 78:1527 (1981).
Oi et al., 'Chimeric Antibodies', *BioTechniques* 4:214 (1986).
Office Action dated Dec. 10, 2014 in U.S. Appl. No. 14/132,607.
Padlan, 'A Possible Procedure for Reducing the Immunogenicity of Antibody Variable Domains While Preserving Their Ligand-Binding Properties', Molecular Immunology 28(4/5):489-498 (1991).
Parra et al., 'Tissue inhibitor of metalloproteinase-1 is increased in the saphenofemoral junction of patients with varices in the leg', J. Vasc. Surg. 28:669-675 (1998).
Patten et al., 'Applications of DNA shuffling to pharmaceuticals and vaccines', 1997, Curr. Opinion Biotechnol. 8:724-33.
Peterson et al., 'Enzymatic Cleavage of Peptide-Linked Radiolabels from Immunoconjugates', 1999, Bioconjug Chem 10:553.
Phizicky et al., 'Protein-protein interactions: methods for detection and anlysis', *Microbiol. Rev.* 59:94-123 (1995).
Polak et al., Introduction to Immunocytochemistry, 2nd ed., Springer Verlag, NY, 1997.
Presta et al., 'Engineering therapeutic antibodies for improved function', 2002, Biochem Soc Trans 30:487-490.
Proudfoot, 'Transcriptional interference and termination between duplicated α-globin gene constructs suggests a novel mechanism for gene reguqaltion', *Nature* 322:562 (1986).
Quinlan TR et al., (1994) Oxygen radicals and asbestos-mediated disease. (Translated from eng) Environ Health Perspect 102 Suppl 10:107-110 (in eng).
Reddy et al, 'Elimination of Fc Receptor-Dependent Effector Functions of a Modified IgG4 Monoclonal Antibody to Human CD4', 2000, J Immunol 164:1925-1933.
Pennington, 'Solid-Phase Synthesis of Peptides Containing the CH2NH Reduced Bond Surrogate', 1994 *Meth Mol Bio* 35:241-247.
Riechmann et al., 'Reshaping human antibodies for therapy', *Nature* 332:323 (1988).
Roguska. et al., 'Humanization of murine monoclonal antibodies through variable domain resurfacing', *PNAS* 91:969-973 (1994).
Rongen et al., 'Liposomes and immunoassays', J. Immunol. Methods 204:105-133 (1997).
Ruther et al., 'Easy identification of cDNA clones', *EMBO J.* 2:1791 (1983).
Santerre et al., 'Expression of prokaryotic genes for hygromycin B and G418 resistance as dominant-selection markers in mouse L cells', *Gene* 30:147 (1984).
Sawai et al., 'Direct Production of the Fab Fragment Derived From the Sperm Immobilizing Antibody Using Polymerase Chain Reaction and cDNA Expression Vectors', *AJRI* 34:26-34 (1995).
Schaffer et al., 'Improving the accuracy of PSI-BLAST protein database searches with composition-based statistics and other refinements', Nucleic Acids Res., 29:2994-3005 (2001).
Schmalzing et al., 'Capillary electrophoresis based immunoassays: A critical review', Electrophoresis 18:2184-93 (1997).
Schneider, 'MSI Offers Drug Discovery Software', *Genetic Engineering News* December: p. 20 (1998).
Self et al., 'Advances in immunoassay technology', Curr. Opin. Biotechnol. 7:60-65 (1996).
Shields et al., 'High Resolution Mapping of the Binding Site on Human IgG1 for FcgRI, FcgRII, FcgRIII, and FcRn and Design of IgG1 Variants with Improved Binding to the FcgR', 2001, J Biol Chem 276:6591-6604.
Shields, R. L. et al., 'Lack of Fucose on Human IgG1 N-Linked Oligosaccharide Improves Binding to Human Fc RIII and Antibody-dependent Cellular Toxicity', (2002) *J. Biol. Chem.* 277:26733-26740.
Shu et al., 'Secretion of a single-gene-encdoed immunoglobulin from myeloma cells', *PNAS* 90:7995-7999 (1993).
Sitia G et al., (2007), "Treatment with HMGB1 inhibitors diminishes CTL-induced liver disease in HBV transgenic mice," J Leukoc Biol 81: 100-7.
Skerra et al., 'Assembly of a Functional Immunoglobllin Fv Fragment in *Escherichia coli'*, *Science* 240:1038-1040 (1988).
Sowdhamini et al., 'Structural and functional analogy between pneumolysin and proaerolysin', *Protein Engineering* 10:207, 215 (1997).
Sporn et al, 'Chemoprevention of Cancer,', Carcinogenesis, vol. 21 (2000), 525-530.
Studnicka et al., 'Human-engineered monoclonal antibodies retain full specific binding activity by preserving non-CDR complementaritu-modulation residues', *Protein Engineering* 7(6):805-814 (1994).
Szybalska & Szybalski, 'Genetics of Human Cell Lines, IV. DNA-Mediated Heritable Transformation of a Biochemical Trait', *Proc. Natl. Acad. Sci. USA* 48:202 (1992).
Takahashi et al., 'Human Fas ligand: gene structure, chromosomal location and species specificity', *Int. Immunol.*, 6:1567-1574 (1994).

(56) References Cited

OTHER PUBLICATIONS

Tempczyk et al., 'Solutions of Ill-posed Problems', *Molecular Simulations Inc. Solutions* Apr. 1997.
Tempest et al., 'Reshaping A Human Monoclonal Antibody to Inhibit Human Respiratory Syncytial Virus Infection In Vivo', *Biotechnology* 9:266-273, 1991.
Thorpe, 'Antibody Carriers of Cytotoxic Agents in Cancer Therapy: A Review', in Monoclonal Antibodies '84: Biological and Clinical Applications, Pinchera et al. (eds.), pp. 475-506 (1985).
Thorpe et al., "The Preparation and Cytotoxic Properties of Antibody-Toxin Conjugates", *Immunol. Rev.* 62:119-58 (1982).
Tietze et al., 'Domino reactions for library synthesis of small molecules in combinatorial chemistry', Curr. Opin. Chem. Biol. 2:363-371, 1998.
Tolstoshev, 'Gene Therapy, concepts, Current Trials and Future Directions', *Ann. Rev. Pharmacol. Toxicol.* 32:573-596 (1993).
Tutt, et al., 'Trispecific F(ab')3 Derivatives That Use Cooperative Signaling Via the TCR/CD3 Complex and CD2 to Activate and Reidirect Resting Cytotoxic T Cells', J. Immunol. 147:60-69 (1991).
Ulloa L, et al., High-mobility group box 1 (HMGB1) protein: friend and foe. *Cytokine Growth Factor Rev.* 2006;17:189-201.
Umana et al. 'Engineered glycoforms of an antineuro-blastoma IgG1 with optimized antibody-dependent cellular cytotoxic activity', (1999) *Nat. Biotech.* 17:176-1.
Vajdos et al., 'Comprehensive Functional Maps of the Antigen-binding Site of an Anti-ErB2 Antibody Obatined with Shotgun Scanning Mutagenesis', (J Mol Biol. Jul. 5, 2002;320(2):415-28 at 416).
Van Heeke et al., 'Expression of Human Asparagine Synthetase in *Escherichia coli*', *J. Biol. Chem.* 24:5503-5509 (1989).
Van Holde, K.E., 'X-Ray Diffraction', Physical Biochemistry, Prentice-Hall, N.J. pp. 221-239 (1971).
Vaughn et al., 'Human Antibodies with Sub-nanomolar Affinities Isolated from a Large Non-immunized Phage Display Library', 1996, Nature Biotechnology, 14(3):309-314.
Vie et al., 'Human fusion proteins between interleukin 2 and IgM heavy chain are cytotoxic for cells expressing the interleukin 2 receptor', 1992, Proc. Natl. Acad. Sci. USA 89:11337-11341.
Weinstein, B., 'Peptide Backcone Modifications: A Structure-Activity Analysis of Peptides Containing Amide Bond Surrogates, Conformational Constraints, and Rela', 1983 *Chemistry & Biochemistry of Amino Acids, Peptides and Proteins* vol. 7, pp. 267-357, Marcel Dekker, Inc., New York.
Wells, 'Systematic Mutational Analyses of Protein-Protein Interfaces', Methods in Enzymol. 202:390-411 (1991).
Wendling, P., "Erionite Deposits in Western U.S. Raise Concern", Rheumatology News, Feb. 2011.
Wigler et al., 'Transfer of Purified Herpes Vuris Thymidine Kinase Gene to Cultured Mouse Cells', *Cell* 11:223 (1977).
Wigler et al., 'Transformation of mammalian cells with an amplifiable dominant-acting gene', Proc Natl. Acad. Sci. USA 77:357 (1980).
Wilson et al., 'The Structure of an Antigenic Determinant in a Protein', *Cell* 37:767 (1984).
Wu and Wu, 'Delivery systems for gene therapy', Biotherapy 3:87-95 (1991).
Xu et al., 'In Vitro Characterization of Five Humanized OKT3 Effector Function Variant Antibodies', 2000, Cell Immunol 200:16-26.
Yang H, et al., 'Programmed necrosis induced by asbestos in human mesothelial cells causes high-mobility group box 1 protein release and resultant inflammation', Proc Natl Acad Sci USA. 2010;107(28):12611-12616.
Yang H, et al., 'TNF-α inhibits asbestos-induced cytotoxicity via a NF-κB-dependent pathway, a possible mechanism for asbestos-induced oncogenesis.', *Proc Natl Acad Sci USA*. 2006; 103(27):10397-10402.
Young KH, 'Yeast Two-Hybrid: SO Many Interactions, (in) So Little Time . . . ', *Biol. Reprod.* 58:302-311 (1998).
Zheng et al., 'Administration of Noncytolytic IL-10/Fc in Murine Models of Lipopolysaccharide-Induced Septic Shock and Allogeneic Islet Transplantation', 1995, J. Immunol. 154:5590-5600.
Zimmerman et al., 'A Triglyceride Linker Improves Tumor Uptake and Biodistributions of 67-Cu-Labeled Anti-Neuroblastoma Mab chCE7 F9ab')2 Fragments', 1999, Nucl Med Biol 26:943.
Office Action dated Jul. 30, 2015 in U.S. Appl. No. 14/123,607.
Advisory Action dated Nov. 19, 2015 in U.S. Appl. No. 14/123,607.
Jube et al., "Abstract 2600: HMGB1, a potential new target for mesothelima therapy", Cancer Res., Apr. 15, 2011, 71:2600.

* cited by examiner

SEQUENCE LISTING

```
<160> NUMBER OF SEQ ID NOS: 3

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60
```

```
Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
                180                 185                 190

Asp Glu Glu Asp Glu Glu Glu Asp Glu Glu Asp Glu Asp
            195                 200                 205

Glu Glu Asp Asp Asp Asp Glu
        210                 215

<210> SEQ ID NO 2
<211> LENGTH: 215
<212> TYPE: PRT
<213> ORGANISM: Homo sapiens

<400> SEQUENCE: 2

Met Gly Lys Gly Asp Pro Lys Lys Pro Thr Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
             35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Leu Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
                180                 185                 190

Asp Glu Glu Asp Glu Glu Glu Asp Glu Glu Asp Glu Glu Asp
            195                 200                 205

Glu Glu Asp Asp Asp Asp Glu
        210                 215
```

```
<210> SEQ ID NO 3
<211> LENGTH: 77
<212> TYPE: PRT
<213> ORGANISM: Homo sapiens

<400> SEQUENCE: 3

Pro Thr Gly Lys Met Ser Ser Tyr Ala Phe Phe Val Gln Thr Cys Arg
 1               5                  10                  15

Glu Glu His Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
65                  70                  75
```

BIOMARKER OF ASBESTOS EXPOSURE AND MESOTHELIOMA

REFERENCE TO RELATED APPLICATIONS

This application is the U.S. National Phase of International Application PCT/US2012/041428, filed Jun. 7, 2012, and claims priority to U.S. Provisional Application Nos. 61/494,340, filed Jun. 7, 2011 and 61/502,283, filed Jun. 28, 2011. Each of the priority applications is hereby incorporated by reference in its entirety.

STATEMENT REGARDING FEDERALLY SPONSORED R&D

This invention was made with Government support under Grant No. R01 CA106567 and P01 CA114047, awarded by the National Cancer Institute. The Government has certain rights in this invention.

The present application is being filed along with a Sequence Listing in electronic format. The Sequence Listing is provided as a file Sequence_Listing-UOH_044NP.TXT, created and last modified on Jan. 24, 2014, which is 4,730 bytes in size. The information in the electronic format of the Sequence Listing is incorporated herein by reference in its entirety.

FIELD

This application relates generally to the field of cancer biology, pathology, and diagnostics. Several embodiments provided herein relate to methods of diagnosing asbestos exposure or mesothelioma. Several embodiments also relate to methods of differentiating whether a tumor of the lung is lung cancer or mesothelioma.

BACKGROUND

In the US, asbestos causes ~2-3,000 malignant mesothelioma (MM) deaths/year, and contributes to an even larger number of lung carcinomas because asbestos has a synergistic carcinogenic effect with cigarette smoke. The latency of 30-50 years from the time of exposure to tumor development could potentially allow time for intervention to block the presently unclear mechanism(s) that trigger asbestos-induced carcinogenesis (Carbone M & Bedrossian C W (2006) The pathogenesis of mesothelioma. (Translated from eng) Semin Diagn Pathol 23(1):56-60 (in eng)).

Asbestos refers to a family of mineral fibers that includes crocidolite, often considered the most oncogenic type. Since asbestos does not induce malignant transformation of primary human mesothelial cells (HM) directly, indirect mechanisms of carcinogenesis have been investigated. Inhaled asbestos fibers become entrapped in the lung and some migrate through the lymphatics to the pleura.

Indeed, cancer often arises in the setting of chronic inflammation and it has been suggested that asbestos-induced inflammation might be somehow linked to asbestos carcinogenesis (Quinlan T R, Marsh J P, Janssen Y M, Borm P A, & Mossman B T (1994) Oxygen radicals and asbestos-mediated disease. (Translated from eng) Environ Health Perspect 102 Suppl 10:107-110 (in eng); Choe N, et al. (1997) Pleural macrophage recruitment and activation in asbestos-induced pleural injury. (Translated from eng) Environ Health Perspect 105 Suppl 5:1257-1260 (in eng)).

The mechanisms that trigger the chronic inflammatory response seen in the lungs of asbestos-exposed individuals and in many MM patients are unknown. Macrophages play an important role in this process by releasing mutagenic reactive oxygen species (ROS) and cytokines that support inflammation. Among these cytokines, TNF-α has been identified as a critical mediator of the pathogenesis of asbestos-related disease. TNF-α has been linked to tumor promotion, to fibrosis and asbestosis, to asbestos carcinogenesis and to MM.

Asbestos is cytotoxic. Most HM exposed to asbestos die within 24-48 hrs. The mechanisms of asbestos-induced HM cell death and the possible link between cytotoxicity and carcinogenesis is unclear.

SUMMARY

The present inventors have surprisingly and unexpectedly discovered that HMGB1 is highly expressed in malignant mesothelioma (MM) tissues and sera of MM patients and subjects exposed to asbestos. Currently, there is no serum marker for asbestos exposure and determining whether a subject has been exposed to asbestos is usually based on the subject's occupational history and personal statement. Furthermore, mesothelioma is difficult to detect with current methods. Furthermore, the present inventors have discovered that mesothelioma have high levels of HMGB1 whereas lung cancers have low levels of HMGB1. Mesothelioma is known to be hard to diagnose, especially because of the difficulty of distinguishing between mesothelioma from lung cancer.

Accordingly, some embodiments relate to methods of diagnosing mesothelioma. Also, some embodiments relate to methods for diagnosing or detecting exposure to asbestos. Still further embodiments relate to methods for distinguishing, differentiating or diagnosing lung neoplasms, for example, lung cancer from mesothelioma.

In one embodiment, a method of diagnosing mesothelioma in a subject can include, for example, contacting a biological sample of the subject with an antibody specific for HMGB1, determining the level of HMGB1 in the sample, and diagnosing the subject as having mesothelioma when the level of HMGB1 in the sample is greater than or falls within a predetermined level.

In another embodiment, a method of diagnosing asbestos exposure in a subject may include, for example, contacting a biological sample of the subject with an antibody specific for HMGB1, determining the level of HMGB1 in the sample, and diagnosing the subject as having been exposed to asbestos when the level of HMGB1 in the sample is greater than or falls within a predetermined level.

In one aspect of the above embodiments, the sample can be for example, a fluid. In another aspect, the sample may be serum, for example. In a further aspect, the predetermined level may be based, for example, on the level of HMGB1 in a healthy control subject. In an additional aspect, the predetermined level can be based, for example, on the level of HMGB1 in a subject not exposed to asbestos. In yet another aspect, the predetermined level may be based, for example, on the level of HMGB1 in a subject not having mesothelioma.

In a further aspect, the sample can be serum and the predetermined level of HMGB1 can be, for example, between about 0-100 ng/mL, between about 0-75 ng/mL, between about 0-50 ng/mL, between about 0-25 ng/mL, or between about 0-10 ng/mL. In another aspect, the level of HMGB1 may be determined, for example, by ELISA.

In an additional embodiment, a method of differentiating whether a tumor of the lung is lung cancer or mesothelioma can include, for example, contacting the tumor with an antibody specific for HMGB1, determining the level of HMGB1 in the tumor, and differentiating whether the tumor is lung cancer or mesothelioma based on the level of HGMB1 in the tumor compared to a predetermined level. In some aspects, the tumor may be identified as lung cancer when the determined level of HMGB1 in the tumor is less than the predetermined level, for example, and the tumor may be identified as mesothelioma when the determined level of HMGB1 in the tumor is greater than the predetermined level, for example.

In several aspects, the lung cancer can be small cell lung cancer, non-small cell lung cancer, or lung adenocarcinoma. In a further aspect, the tumor can be a biopsy from a subject. In another aspect, the level of HMGB1 in the tumor may be determined by immunohistochemistry, for example.

BRIEF DESCRIPTION OF THE DRAWINGS

FIG. 1A shows immunohistochemical analysis of HMGB1 and RAGE expression in MM biopsies. FIG. 1B shows immunohistochemical analysis of HMGB1 expression in lung cancer biopsies tissues. FIG. 1C is a graph showing HMGB1 levels in sera of MM patients and normal individuals measured by ELISA.

FIG. 4A is a graph showing qPCR measurements of HMGB1 mRNA transcript levels. FIG. 4B is a graph showing qPCR measurements of RAGE mRNA transcript levels. FIG. 4C is a Western Blot and graph comparing levels of HMGB1 in normal human mesothelial (HM) cells and MM cells. FIG. 4D is a Western Blot and graph comparing levels of RAGE in normal human mesothelial (HM) cells and MM cells. FIG. 4E is a panel of immunocytochemistry images showing a comparison of HMGB1 protein in HM cells and MM cells. FIG. 4F is a graph showing positive correlation between HMGB1 and RAGE transcript levels in five different MM cell lines tested (r=0.93, P=0.022). FIG. 4G is a graph showing the amount of HMGB1 released by in vitro cell cultures measured by ELISA.

FIG. 5A shows HMGB1 translocates from the nucleus to the cytosol upon asbestos exposure: Top row, HMGB1 staining (FITC conjugated antibody, green); middle row, DAPI staining (blue); bottom row, overlay of HMGB1 (green) and DAPI staining (blue). FIG. 5B is a Western Blot that shows HMGB1 is released from HM after asbestos exposure. FIG. 5C is a Western Blot that shows HMGB1 is released from HM into the extracellular medium during asbestos exposure.

DETAILED DESCRIPTION

Figure 1:
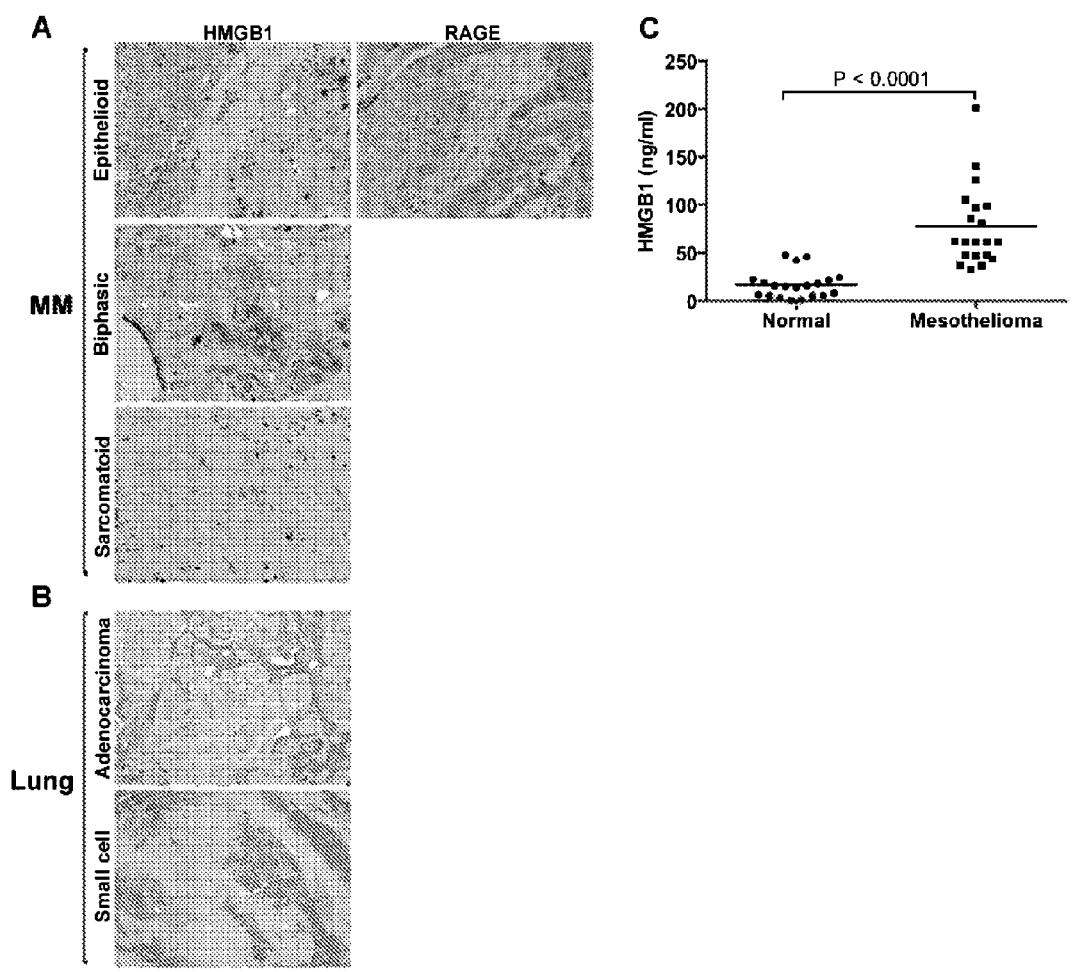
FIG. 1 shows HMGB1 is highly expressed in malignant mesothelioma (MM) tissues and sera of MM patients.

Provided herein are embodiments based on the surprising and unexpected discovery that HMGB1 is highly expressed in malignant mesothelioma (MM) tissues and sera of MM patients and subjects exposed to asbestos. Also provided herein are embodiments drawn to the discovery that mesothelioma have high levels of HMGB1 whereas lung cancers have low levels of HMGB1.

Several embodiments provided herein relate to methods of detecting and diagnosing asbestos exposure or mesothelioma. Some aspects of the aforementioned embodiments can include, for example, contacting a biological sample (such as serum) of a subject with an antibody specific for the High Mobility Group Box 1 (HMGB1) protein and diagnosing the subject as having mesothelioma or having been exposed to asbestos when the level of HMGB1 in the sample is greater than a predetermined level. Various other embodiments relate to methods of differentiating whether a tumor of the lung is lung cancer or mesothelioma. In some aspects, such methods can include contacting a tumor, such as a tumor biopsy from a subject, with an antibody specific for HMGB1 and differentiating whether the tumor is lung cancer or mesothelioma based on the determined level of HMGB1 relative to a predetermined level.

HMGB1 is a damage associated molecular pattern (DAMP) molecule and a mediator of chronic inflammation (Bianchi M E (2007) DAMPs, PAMPs and alarmins: all we need to know about danger. J Leukoc Biol 81: 1-5; 13-15; which is incorporated herein by reference in its entirety). HMGB1 is actively secreted by macrophages and dendritic cells (DCs) and passively released by cells undergoing necrosis. HMGB1 is a nuclear protein, but can be detected in the cytoplasm of cells undergoing necrosis and in cells that actively secrete HMGB1, such as macrophages. HMGB1 binds to the Receptor for Advanced Glycation Endproducts (RAGE) and to the Toll-like Receptors (TLRs) 2 and 4, responsible for inflammatory responses. The activation of RAGE by HMGB1 induces tumor cell proliferation, migration, and invasion. HMGB1 induces migration in certain cell types.

Diagnosing Asbestos Exposure or Mesothelioma

Several embodiments provided herein are drawn to the surprising and unexpected discovery that HMGB1 is highly expressed in malignant mesothelioma (MM) tissues and sera of MM patients and subjects exposed to asbestos. Currently, there is no serum marker for asbestos exposure and determining whether a subject has been exposed to asbestos is usually based on the subject's occupational history and personal statement. Furthermore, mesothelioma is difficult to detect with current methods.

Various embodiments provided herein relate to methods of diagnosing asbestos exposure or mesothelioma in a subject including contacting a biological sample of the subject with an antibody (or fragment thereof that is) specific for HMGB1, determining the level of HMGB1 in the sample, and diagnosing the subject as having been exposed to asbestos or having mesothelioma when the level of HMGB1 in the sample is greater than or within a predetermined level.

Several embodiments relate to methods for diagnosis and prognosis evaluation for mesothelioma. In one aspect, the amount of soluble HMGB1 in a biological sample can be determined in different patient samples for which either diagnosis or prognosis information is desired, to provide profiles. A profile of a particular sample is essentially a "fingerprint" of the state of the sample. A normal state may be distinguished from a mesothelioma state, and within mesothelioma states, different prognosis states (good or poor long term survival prospects, for example) can be determined. Diagnosis may be done or confirmed by comparing patient samples with the known profiles. By assessing the evolution of HMGB1 levels at different times during mesothelioma progression, the stage of mesothelioma can be determined as well as the likely prognosis.

Differentiating Between Lung Cancer and Mesothelioma

Several embodiments provided herein are drawn to the discovery that mesothelioma have high levels of HMGB1 whereas lung cancers have low levels of HMGB1. Mesothelioma is known to be hard to diagnose, especially because of the difficulty of distinguishing between mesothelioma from lung cancer. In fact, it is estimated that mesothelioma is misdiagnosed 10-30% of the time owing to the difficulty of distinguishing between mesothelioma from lung cancer.

Accordingly, various embodiments provided herein relate to methods of differentiating whether a tumor of the lung is lung cancer or mesothelioma including contacting the tumor with an antibody (or fragments thereof that are) specific for HMGB1, determining the level of HMGB1 in the tumor, and differentiating whether the tumor is lung cancer or mesothelioma based on the level of HGMB1 in the tumor compared to a predetermined level, wherein the tumor is identified as lung cancer when the determined level of HMGB1 in the tumor is less than the predetermined level and the tumor is identified as mesothelioma when the determined level of HMGB1 in the tumor is greater than the predetermined level.

DEFINITIONS

As used herein, the terms "mesothelioma" and "malignant mesothelioma" (MM) are used interchangeably. Human malignant mesothelioma (MM) is an aggressive and rapidly lethal cancer often associated with exposure to asbestos. Prognosis is poor, due to late-stage diagnosis and resistance to current therapies. Human malignant mesothelioma (MM) arises from the neoplastic transformation of mesothelial cells lining the pleural peritoneal and (rarely) pericardial cavities, and from the tunica vaginalis testis. MM has been linked to occupational and environmental exposure to asbestos, causing about 3,000 deaths per year in the U.S. and over 100,000 deaths per year worldwide. In the U.S., the incidence of MM is stable since 1994; the incidence of MM is increasing in Europe and in rapidly industrializing countries, such as India and China, where the use of asbestos is rising dramatically. MM is a very aggressive cancer, usually diagnosed at later stages, and is refractory to most therapeutic modalities, leading to poor prognosis and a median survival from diagnosis of 8-12 months.

As used herein, "subject" includes organisms which are capable of suffering from a cancer, such as human and non-human animals. Preferred animals include human subjects. The term "non-human animals" includes all vertebrates, for example, mammals, e.g., rodents (e.g., mice, rats, Guinea Pigs, etc.), rabbits, canines, ruminants (e.g., sheep, cows, etc.), non-human primates, and non-mammals, such as chickens, amphibians, reptiles, etc. In the case of the non-human animals, the subject can be a laboratory animal, including an engineered animal, for example a mouse engineered to have a cancer tissue.

As used herein, a "biological sample" contemplates a sample obtained from an organism or from components (e.g., cells) of an organism, including cell cultures. The sample may be of any biological tissue or fluid, for example. Usually, the sample is a biological or a biochemical sample. Frequently the sample will be a "clinical sample" which is a sample derived from a patient. Such samples include, but are not limited to, sputum, cerebrospinal fluid, blood, blood fractions such as serum including fetal serum (e.g., SFC) and plasma, blood cells (e.g., white cells), tissue or fine needle biopsy samples, urine, peritoneal fluid, and pleural fluid, or cells there from. Biological samples may also include sections of tissues such as frozen sections taken for histological purposes. The sample can be, for example, also a physiological sample. The term "tissue" as used herein refers to cellular material from a particular physiological region. The cells in a particular tissue can comprise several different cell types. A non-limiting example of this would be tumor tissue that comprises capillary endothelial cells and blood cells, all contained in a given tissue section or sample. It will be appreciated from the disclosure and the technology that in addition to solid tissues, the term "tissue" is also intended to encompass non-solid tissues, such as blood. In some instances, the tissue can be or can include cells and cell cultures, including mesothelioma cells and cell cultures, other cancer cells and cultures such as other lung cancers, as well as non-cancerous cells and cell cultures. The cells and cell cultures can be from research cell lines or from a particular subject of interest, for example.

As used herein, a "predetermined level" of HMGB1 refers to a level of HMGB1 in a control sample or standard. A "control sample" or "standard" in turn relates to a sample of which the expression level, amount and/or abundance of HMGB1 is known, or has been determined previously. As such, the control sample may be derived from a "healthy" person, i.e., a person diagnosed previously as not suffering or predisposed from the pathological condition(s) at issue (e.g. mesothelioma). Alternatively, the control sample may be derived from a "diseased" person, i.e. a person diagnosed previously as suffering or predisposed from a disease other than mesothelioma, or a person diagnosed as having mesothelioma at a particular stage. Furthermore, the predetermined level can alternatively reflect an average of multiple control samples or standards (e.g. from a control population or cohort). A control sample or standard can be spiked with a known amount of molecules. In a further alternative, the control sample may be synthetic, i.e. not derived from a person, but comprising a known amount of molecules.

Anti-HMGB1 Antibodies

Several anti-HMGB1 antibodies have been described and are known in the art and can be used in the methods provided herein for diagnosing asbestos exposure or mesothelioma, or differentiating between lung cancer and mesothelioma. For example, numerous high affinity antibodies that specifically bind HMGB1 and antigenic fragments thereof are described in U.S. Patent Application Publication No. 2010/0061987, which is herein incorporated by reference in its entirety. Such antibodies disclosed therein are non-limiting examples of suitable anti-HMGB1 antibodies that can be used in embodiments for preventing or treating cancer provided in this application. For instance, antibodies designated therein as G2, G4 (ATCC#PTA-6258), G9, G12, G16, G20, G34, G35, S2 (ATCC#PTA-6142), S6 (ATCC#PTA-6143), S10, S12, S14, S16, S17, and E11 are examples of known anti-HMGB1 antibodies that can be used in embodiments provided herein.

Additional examples of suitable anti-HMGB1 antibodies are described in U.S. Patent Application Publication No. 2009/0148453, which is herein incorporated by reference in its entirety. For instance, monoclonal antibodies designated therein as 6E6 HMGB1 mAb, 2E11 HMGB1 mAb, 6H9 HMGB1 mAb, 10D4 HMGB1 mAb, 2G7 HMGB1 mAb, 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, and 4A10 HMGB1 mAb can be used in embodiments provided herein.

Furthermore, several anti-HMGB1 antibodies that can be used in embodiments provided herein are commercially available from vendors including Abbiotec (e.g., cat #s 252233, 252169, 250508), Abcam (e.g., HAP 46.5), AbD Serotec (e.g., P09429), Abgent (e.g., AT2384a), Abnova (e.g., H00003146-AP 45), ABR (e.g., KS1), Acris Antibodies GmbH (e.g., J2E1), AdipoGen (e.g., GIBY-1-4), ARP American Research Products (e.g. J2E1), Assay Biotech (e.g. C10316), Enzo Life Sciences, Aviva Systems Biology (e.g., ARP38110_T100), Biorbyt (e.g., orb27349), Cell Signalling Technology (e.g. 3935S), eBioscience (e.g. 14-9900-80), EMD Millipore (e.g., 07-584, MABE148), Epitomics (e.g., S0476), GeneTex (e.g., EPR3506, EPR3507), GenWay Biotech (e.g., 18-003-42680), Immuno-Biological Laboratories (e.g., IBAHM0915), LifeSpan BioSciences (e.g., LS-C36810-50), MBL International (e.g., 4C9), Novus Biologicals (e.g., H00003146), Origene Technologies (e.g., TA301448), Proteintech Group (e.g., 10829-1-AP), R&D Systems (e.g., 115603), Santa Cruz Biotechnology (e.g., J2E1), Sigma-Aldrich (e.g., SAB2101049, SAB4501401, WH0003146M8, SAB1403925, AV35646, AV38110, H9539, H9664), Pierce Antibodies (e.g., PA1-16926; MA1-20338, MA1-90941, etc.), and United States Biological (e.g., H6202-03).

High affinity antibodies of various embodiments can specifically bind a polypeptide comprising or alternatively consisting of a human HMGB1 polypeptide (SEQ ID NO:1 or SEQ ID NO:2; See Table 1). Full-length HMGB1 polypeptides of human and other animals are well known in the art (see, e.g., US20040005316; U.S. Pat. Nos. 6,468,533 and 6,448,223, which are incorporated herein by reference in their entireties).

TABLE 1

Human HMGB1 amino acid sequence (GenBank Acc.
No. NP_002119, all of the information of which is
incorporated herein by reference in its entirety)
(SEQ ID NO: 1)

MGKGDPKKPRGKMSSYAFFVQTCREEHKKKHPDASVNFSEFSKKCSERWK
TMSAKEKGKFEDMAKADKARYEREMKTYIP PKGETKKKFKDPNAPK
RPPSAFFLFCSEYRPKIKGEHPGLSIGDVAKKLGEMWNNTAADDKQPYE
KKAAKLKEKYEKDIAAYRAKGKPDAAKKGVVKAEKSKKKKEEEEDEEDE
EDEEEEEDEEDEDEEE DDDDE

Human HMGB1 amino acid sequence (GenBank ACC.
NO. AAA64970, all of the information of which is
incorporated herein by reference in its entirety)
(SEQ ID NO: 2)

MGKGDPKKPTGKMSSYAFFVQTCREEHKKKHPDASVNFSEFSKKCSERWK
TMSAKEKGKFEDMAKADKARYEREMKTYIPPKGETKKKFKDPNAPKRLPS
AFFLFCSEYRPKIKGEHPGLSIGDVAKKLGEMWNNTAADDKQPYEKKAAK
LKEKYEKDIAAYRAKGKPDAAKKGVVKAEKSKKKKEEEEDEEDEEDEEEE
EDEEDEEDEE DDDDE

In several embodiments, the antibodies that can specifically bind HMGB1 and antigenic fragments thereof can be humanized or human antibodies.

In several embodiments, antibodies can specifically bind HMGB1 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M or of less than $10^{-11}$ M, or of less than $10^{-12}$ M or of less than $10^{-13}$ M.

In another embodiment, the antibody can bind to HMGB1 and/or antigenic fragments thereof with a $K_{off}$ of less than $1\times10^{-3}$ s$^{-1}$. In other embodiments, the antibody binds to HMGB1 and antigenic fragments thereof with a $K_{off}$ of less than $10^{-3}$ s$^{-1}$, less than $5\times10^{-3}$ s$^{-1}$, less than $10^{-4}$ s$^{-1}$, less than $5\times10^{-5}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

In another embodiment, the antibody binds to HMGB1 and/or antigenic fragments thereof with an association rate constant or $k_{on}$ rate of at least $10^{-5}$ M$^{-1}$s$^{-1}$, at least $5\times10^{-5}$ M$^{-1}$s$^{-1}$, at least $10^{-6}$ M$^{-1}$s$^{-1}$, at least $5\times10^{-6}$ M$^{-1}$s$^{-1}$, at least $10^{-7}$ M$^{-1}$s$^{-1}$, at least $5\times10^{-7}$ M$^{-1}$s$^{-1}$, or at least $10^{-8}$ M$^{-1}$s$^{-1}$, or at least $10^{-9}$ M$^{-1}$s$^{-1}$.

The high affinity antibodies include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. Thus, it should be understood that in the embodiments described herein that mention an "antibody" or "antibodies," that any of the molecules listed in this paragraph can be substituted for or used in addition to said antibody or antibodies. Any of the compositions of matter listed in this paragraph can be used in any of the methods described herein.

An additional nonexclusive embodiment includes high affinity antibodies that have certain preferred biochemical characteristics such as a particular isoelectric point (pI) or melting temperature (Tm).

In one embodiment, the high affinity antibodies have a pI ranging from 5.5 to 9.5. In one embodiment, the high affinity antibodies of several embodiments have a Tm ranging from about 65° C. to about 120° C.

In various embodiments, antibodies (and fragments thereof) that specifically bind HMGB1 with high affinity which have been deposited with the American Type Culture Collection can be used in the embodiments described herein (10801 University Boulevard, Manassas, Va. 20110-2209) and assigned ATCC Deposit Nos. PTA-6142 (Deposited Aug. 4, 2004), PTA-6143 (Deposited Aug. 4, 2004), PTA-6259 (Deposited Oct. 19, 2004) and PTA-6258 (Deposited Oct. 19, 2004) (also referred to herein as "S2", "S6", "S16", and "G4", respectively).

Other embodiments include particular antibodies (and fragments thereof) that specifically bind HMGB1 with high affinity and comprise at least one of the variable regions disclosed in U.S. Patent Application Publication No. 2010/0061987, which is incorporated herein by reference in its entirety. Antibodies having at least one, at least two, at least three, at least four at least five or at least 6 of the CDRs of the antibodies disclosed therein can be used in embodiments of the present application. Antibodies having at least one, at least two, at least three, at least four, at least five, or all six of the CDRs of the deposited antibodies can be used in various embodiments of the present application.

Further, any antibody that specifically binds the same epitope as the anti-HMGB1 antibodies disclosed in U.S. Patent Application Publication No. 2010/0061987 (incorporated herein by reference in its entirety) can be used in various embodiments. It is contemplated that these antibodies will bind the same epitope as the deposited antibodies with at least equal affinity, or better affinity, or less affinity.

As used herein, the term "antibody" or "high affinity antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. The antibodies of several embodiments provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992); each of which is incorporated herein by reference in its entirety.

Other antibodies specifically contemplated are "oligoclonal" antibodies. As used herein, the term "oligoclonal" antibodies" refers to a predetermined mixture of distinct monoclonal antibodies. Methods for generating oligoclonal antibodies are known in the art. See, e.g., "Examples Section", example 1, PCT publication WO 95/20401; U.S. Pat. Nos. 5,789,208 and 6,335,163; each of which is incorporated herein by reference in its entirety. In certain embodiments, oligoclonal antibodies consist of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618, which is incorporated herein by reference in its entirety). Oligoclonal antibodies are particularly useful when it is desired to target multiple epitopes on a single target molecule (e.g., HMGB1). Those skilled in the art will know or can determine what type of antibody or mixture of antibodies is applicable for an intended purpose and desired need. In particular, antibodies of several embodiments include immunoglobulin molecules and immunologically active portions of immunoglobulin molecules, i.e., molecules that contain an antigen binding site that specifically binds to an HMGB1 antigen (e.g., one or more complementarity determining regions (CDRs) of an anti-HMGB1 antibody). It is also specifically contemplated that the antibodies of several embodiments include immunoglobulin molecules and immunologically active portions of immunoglobulin molecules, i.e., molecules that contain an antigen binding site that specifically binds to an HMGB1 antigen (e.g., one or more complementarity determining regions (CDRs) of an anti-HMGB1 antibody). The immunoglobulin molecules of several embodiments can be of any type (e.g., IgG, IgE, IgM, IgD, IgA and IgY), class (e.g., IgG1, IgG2, IgG3, IgG4, IgA1 and IgA2) or subclass of immunoglobulin molecule Immunoglobulins may have both a heavy and light chain. An array of IgG, IgE, IgM, IgD, IgA, and IgY heavy chains may be paired with a light chain of the kappa or lambda forms.

The antibodies of embodiments provided herein also encompass immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" include full length antibodies and Fc variants thereof comprising Fc regions, or fragments thereof, comprising at least one novel amino acid residue described herein fused to an immunologically active fragment of an immunoglobulin or to other proteins as described herein. Such variant Fc fusions include but are not limited to, scFv-Fc fusions, variable region (e.g., VL and VH)-Fc fusions, scFv-scFv-Fc fusions Immunoglobulin molecules can be of any type (e.g., IgG, IgE, IgM, IgD, IgA and IgY), class (e.g., IgG1, IgG2, IgG3, IgG4, IgA1 and IgA2) or subclass.

Antibodies of several embodiments also encompass those that have half-lives (e.g., serum half-lives) in a mammal, (e.g., a human), of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311 and discussed in more detail below); each of which is incorporated herein by reference in its entirety.

In one embodiment, the antibodies may comprise modifications/substations and/or novel amino acids within their Fc domains such as, for example, those disclosed in Ghetie et al., 1997, Nat. Biotech. 15:637-40; Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. No. 10/370,749 and PCT Publications WO 94/2935; WO 99/58572; WO 00/42072; WO 02/060919, WO 04/029207; each of which is incorporated herein by reference in its entirety. Other modifications/substitutions of the Fc domain will be readily apparent to one skilled in the art.

Antibodies can comprise modifications/substations and/or novel amino acid residues in their Fc regions can be generated by numerous methods well known to one skilled in the art. Non-limiting examples include, isolating antibody coding regions (e.g., from hybridoma) and making one or more desired substitutions in the Fc region of the isolated antibody coding region. Alternatively, the variable regions of an antibody may be subcloned into a vector encoding an Fc region comprising one or modifications/substations and/or novel amino acid residues.

Antibodies of several embodiments may also be modified to alter glycosylation, again to alter one or more functional properties of the antibody.

In various embodiments, the glycosylation of the antibodies can be modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861; each of which is incorporated herein by reference in its entirety.

Additionally or alternatively, an antibody of several embodiments can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342; each of which is incorporated herein by reference in its entirety.

The antibodies of several embodiments can be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387; each of which is incorporated herein by reference in its entirety.

Antibodies provided herein can include derivatives that are modified, i.e., by the covalent attachment of any type of molecule to the antibody such that covalent attachment does not prevent the antibody from binding an HMGB1 polypeptide or fragment thereof and/or generating a desired response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In several embodiments, the high affinity antibodies specifically bind a polypeptide comprising, or alternatively consisting of (or consisting essentially of) an HMGB1 polypeptide having at least 60% identity, or at least 70% identity, or at least 80% identity, at least 85% identity, at least 90% identity, at least 95% identity, at least 96% identity, at least at least 97% identity, at least 98% identity, or at least 99% identity, or 100% identity to the human HMGB1 polypeptide of SEQ ID NO:1 or 2.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. When utilizing BLAST and Gapped BLAST programs, the default parameters of the respective programs (e.g., BLASTN) can be used. See http://www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Several embodiments include particular antibodies (and fragments thereof) that bind HMGB1 with high affinity and are designated "S2", "S6", "S16" and "G4," which have been deposited under the Budapest Treaty with the American Type Culture Collection (ATCC, 10801 University Boulevard, Manassas, Va. 20110-2209) and assigned ATCC Deposit Nos. PTA-6142, PTA-6143, PTA-6259 and PTA-6258, respectively, which are incorporated herein by reference in their entireties.

Several embodiments include particular antibodies designated 6E6 HMGB1 mAb, 2E11 HMGB1 mAb, 6H9 HMGB1 mAb, 10D4 HMGB1 mAb, 2G7 HMGB1 mAb, 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, and 4A10 HMGB1 mAb as described in U.S. Patent Application Publication No. 2009/0148453, which is incorporated herein by reference in its entirety.

Several embodiments also encompass variants of the above described known antibodies comprising one or more amino acid residue substitutions in the variable light ($V_L$) domain and/or variable heavy ($V_H$) domain. Several also encompasse variants of the above described known antibodies with one or more additional amino acid residue substitutions in one or more $V_L$ CDRs and/or one or more $V_H$ CDRs. The antibody generated by introducing substitutions in the $V_H$ domain, $V_H$ CDRs, $V_L$ domain and/or $V_L$ CDRs of the above described known antibodies can be tested in vitro and in vivo, for example, for its ability to bind to HMGB1 (by, e.g., immunoassays including, but not limited to ELISAs and BIAcore), or for its ability to inhibit HMGB1-induced cytokine release, prevent or treat cancer as described herein.

In other embodiments, antibodies can have at least one, at least two, at least three, at least four, at least five, or at least six of the CDRs of the known antibodies described above.

Various embodiments include antibodies that specifically bind to HMGB1 comprising derivatives of the $V_H$ domains, V$_H$ CDRs, V$_L$ domains, or V$_L$ CDRs described in U.S. Patent Application Publication Nos. 2010/0061987 and 2009/0148453 (incorporated herein in their entireties) that specifically bind to HMGB1. Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis are routinely used to generate amino acid substitutions. In one embodiment, the V$_H$ and/or V$_L$ CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions in the relative to the original V$_H$ and/or V$_L$ CDRs. In another embodiment, the V$_H$ and/or V$_L$ CDRs derivatives have conservative amino acid substitutions (e.g. supra) are made at one or more predicted non-essential amino acid residues (i.e., amino acid residues which are not critical for the antibody to specifically bind to HMGB1). Alternatively, mutations can be introduced randomly along all or part of the V$_H$ and/or V$_L$ CDR coding sequence, such as by saturation mutagenesis, and the resultant mutants can be screened for biological activity to identify mutants that retain activity. Following mutagenesis, the encoded antibody can be expressed and the activity of the antibody can be determined.

Several embodiments also encompass antibodies that specifically bind to HMGB1 or a fragment thereof, said antibodies comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% or 100% identical to the amino acid sequence of the variable heavy chain and/or light chain of any of the known above described antibodies.

Various embodiments further encompass antibodies that specifically bind to HMGB1 or a fragment thereof, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, 96%, 97%, 98%, or at least 99% or even 100% identical to the amino acid sequence of one or more CDRs of the known above described antibodies. The determination of percent identity of two amino acid sequences can be determined by any method known to one skilled in the art, including BLAST protein searches.

Another embodiment includes the introduction of conservative amino acid substitutions in any portion of an anti-HMGB1 antibody described herein. It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 2.

TABLE 2

Families of Conservative Amino Acid Substitutions

| Family | Amino Acids |
| --- | --- |
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

The term "conservative amino acid substitution" also refers to the use of amino acid analogs or variants.

Methods of Generating Antibodies

High affinity antibodies or fragments that specifically bind to an HMGB1 polypeptide can be identified, for example, by immunoassays, BIAcore, or other techniques known to those of skill in the art.

The antibodies of several embodiments may be generated by any suitable method known in the art. Polyclonal antibodies to an antigen-of-interest can be produced by various procedures well known in the art. For example, an HMGB1 polypeptide can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981); each of which is incorporated herein by reference in its entirety. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. A "monoclonal antibody" may comprise, or alternatively consist of, two proteins, i.e., a heavy and a light chain.

Methods for producing and screening for specific antibodies using hybridoma technology are routine and well known in the art. In a non-limiting example, mice can be immunized with a HMGB1 polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a HMGB1 polypeptide. Ascites fluid, which generally contains high levels of antibodies, can be generated by immunizing mice with positive hybridoma clones.

Accordingly, several embodiments provide methods of generating monoclonal antibodies as well as antibodies produced by the method comprising culturing a hybridoma cell secreting an antibody wherein the hybridoma is generated by fusing splenocytes isolated from a mouse immunized with a HMGB1 antigen with myeloma cells and then screening the hybridomas resulting from the fusion for hybridoma clones that secrete an antibody able to bind a HMGB1 polypeptide.

Antibody fragments which recognize specific epitopes may be generated by known techniques. For example, Fab and F(ab')2 fragments of several embodiments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of various embodiments can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of several embodiments include those disclosed in PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988); each of which is incorporated herein by reference in its entirety.

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988); each of which is incorporated herein by reference in its entirety.

For some uses, including in vivo use of antibodies in humans and in vitro detection assays, it may be desirable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397; each of which is incorporated herein by reference in its entirety. Humanized antibodies are antibody molecules from non-human species antibody that bind the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988); each of which is incorporated herein by reference in its entirety). Antibodies can be humanized using a variety of techniques known in the art including, for example, CDR-grafting (EP 239,400; PCT publication WO 91/09967; U.S. Pat. Nos. 5,225,539; 5,530,101; and 5,585,089; each of which is incorporated herein by reference in its entirety), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332); each of which is incorporated herein by reference in its entirety.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a HMGB1 polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995), which is incorporated herein by reference in its entirety. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; each of which is incorporated herein by reference in its entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988), which is incorporated herein by reference in its entirety).

Further, antibodies to HMGB1 polypeptides can, in turn, be utilized to generate anti-idiotype antibodies that "mimic" HMGB1 polypeptides using techniques well known to those skilled in the art (See, e.g., Greenspan & Bona, *FASEB J.* 7(5):437-444; (1989) and Nissinoff, *J. Immunol.* 147(8): 2429-2438 (1991); each of which is incorporated herein by reference in its entirety).

Phage display technology can also be utilized to select antibody genes with binding activities towards the polypeptide either from repertoires of PCR amplified v-genes of lymphocytes from humans screened for possessing anti-B box antibodies or from naive libraries (McCafferty et al., *Nature* 348:552-554, 1990; and Marks, et al., *Biotechnology* 10:779-783, 1992, which is incorporated herein by reference in its entirety). The affinity of these antibodies can also be improved by chain shuffling (Clackson et al., *Nature* 352: 624-628, 1991, which is incorporated herein by reference in its entirety).

The choice of polypeptide to be used for the generation can be readily determined by one skilled in the art. Polypeptides may be chosen such that the antibody generated will not significantly cross-react or specifically bind to another member of the HMG protein family. Alternatively, polypeptides which share a large degree of homology between two or more members of the HMG protein family may be used for the generation of an antibody that can specifically bind (i.e., cross-react) with multiple members of the HMG protein family (e.g., HMGB1 and HMG2).

Methods of Producing Antibodies

The antibodies of several embodiments can be produced by any method known in the art for the synthesis of antibodies, in particular, by chemical synthesis or preferably, by recombinant expression techniques.

Recombinant expression of an antibody or fragment, derivative or analog thereof, (e.g., a heavy or light chain of an antibody or a single chain antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Various embodiments thus provide replicable vectors comprising a nucleotide sequence encoding an antibody molecule, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464; each of which is incorporated herein by reference in its entirety) and the variable domain of the antibody may be cloned into such a vector for expression of the entire heavy or light chain.

The expression vector is transferred to a host cell by conventional techniques and the transfected cells are then cultured by conventional techniques to produce an antibody. Thus, several embodiments include host cells containing a polynucleotide encoding an antibody, or a heavy or light chain thereof, or a single chain antibody, operably linked to a heterologous promoter. Vectors encoding both the heavy and light chains may be co-expressed in the host cell for expression of the entire immunoglobulin molecule, as detailed below.

A variety of host-expression vector systems may be utilized to express the antibody molecules described herein. Such host-expression systems represent vehicles by which the coding sequences of interest may be produced and subsequently purified, but also represent cells which may, when transformed or transfected with the appropriate nucleotide coding sequences, express an antibody molecule in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, 3T3, PerC6 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)). Also see, e.g., U.S. Pat. Nos. 5,827,739, 5,879,936, 5,981,216, and 5,658,759; each of which is incorporated herein by reference in its entirety.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), which is incorporated herein by reference in its entirety, in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)), each of which is incorporated herein by reference in its entirety; and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA* 81:355-359 (1984), which is incorporated herein by reference in its entirety). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987), which is incorporated herein by reference in its entirety).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, NS0, Per.C6 and in particular, breast cancer cell lines such as, for example, BT483, Hs578T, HTB2, BT20 and T47D, and normal mammary gland cell lines such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Proc Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 Clinical Pharmacy 12:488-505; Wu and Wu, Biotherapy 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, 1993, *TIB TECH* 11(5):155-215); and hygro, which confers resistance to hygromycin (Santerre et al., *Gene* 30:147 (1984), each of which is incorporated herein by reference in its entirety). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), each of which is incorporated herein by reference in its entirety.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987), which is incorporated herein by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983), which is incorporated herein by reference in its entirety).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:562 (1986); Kohler, *Proc. Natl. Acad. Sci. USA* 77:2197 (1980), which is incorporated herein by reference in its entirety). The coding sequences for the heavy and light chains may comprise cDNA or genomic DNA.

Once an antibody molecule has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies or fragments thereof can be fused to heterologous polypeptide sequences described herein or otherwise known in the art, to facilitate purification.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), which is incorporated herein by reference in its entirety, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984), which is incorporated herein by reference in its entirety) and the "flag" tag.

The antibodies described herein include derivatives that are modified (e.g., by the covalent attachment of any type of molecule to the antibody). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Various embodiments encompass the use of antibodies or fragments thereof recombinantly fused or chemically conjugated (including both covalent and non-covalent conjugations) to a heterologous protein or polypeptide (or fragment thereof, specifically to a polypeptide of at least 10, at least 20, at least 30, at least 40, at least 50, at least 60, at least 70, at least 80, at least 90 or at least 100 amino acids) to generate fusion proteins. In some embodiments, the antibodies or fragments thereof can be recombinantly fused or chemically conjugated (including both covalent and non-covalent conjugations) to a heterologous protein or polypeptide (or fragment thereof, specifically to a polypeptide of at least about 10, at least about 20, at least about 30, at least about 40, at least about 50, at least about 60, at least about 70, at least about 80, at least about 90 or at least about 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, each of which is incorporated herein by reference in its entirety.

Several embodiments include formulations comprising heterologous proteins, peptides or polypeptides fused or conjugated to antibody fragments. For example, the heterologous polypeptides may be fused or conjugated to a Fab fragment, Fd fragment, Fv fragment, F(ab)2 fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341, each of which is incorporated herein by reference in its entirety.

Additional fusion proteins, e.g., of antibodies that specifically bind HMGB1 or fragments thereof (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313, each of which is incorporated herein by reference in its entirety. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to a C/CLP may be recombined with one or more components, motifs, sections, parts, domains, fragments, etc. of one or more heterologous molecules.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, which is incorporated herein by reference in its entirety, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767, which is incorporated herein by reference in its entirety) and the "flag" tag.

Various embodiments further encompass antibodies or fragments thereof conjugated to a diagnostic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900, which is incorporated herein by reference in its entirety, for metal ions which can be conjugated to antibodies for use as diagnostics. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include but are not limited to, $^{125}$I, $^{131}$I, $^{111}$In or $^{99}$Tc, in addition positron emitting metals using various positron emission tomographies, nonradioactive paramagnetic metal ions, and molecules that are radiolabelled or conjugated to specific radioisotopes can be conjugated to the antibodies described herein.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Detectable Labels

In several embodiments, the antibodies are labeled with a detectable label. The detectable labels can be primary labels (where the label comprises an element that is detected directly or that produces a directly detectable element) or secondary labels (where the detected label is attached to a second binding component that can bind to the binding component that binds to the oligosaccharide determinant. An introduction to labels, labeling procedures and detection of labels is found in Polak and Van Noorden (1997) Introduction to Immunocytochemistry, 2nd ed., Springer Verlag, NY and in Haugland (1996) Handbook of Fluorescent Probes and Research Chemicals, a combined handbook and catalogue published by Molecular Probes, Inc., Eugene, Oreg.; each of which is herein incorporated by reference in its entirety. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocyanate (TRITC), etc.), digoxigenin, biotin, phycoerythrin, AMCA, CyDyes™, and the like), radiolabels (e.g., 3H, 125I, 35S, 14C, 32P, 33P, etc.), enzymes (e.g., horse radish peroxidase, alkaline phosphatase etc.), spectral colorimetric labels such as colloidal gold or colored glass or plastic (e.g., polystyrene, polypropylene, latex, etc.) beads. The label may be coupled directly or indirectly to an antibody according to methods well known in the art. As indicated above, a wide variety of labels may be used, with the choice of label depending on sensitivity required, ease of conjugation with the compound, stability requirements, available instrumentation, and disposal provisions.

Suitable labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologiesi Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Enzymes that can be conjugated to antibodies provided herein include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl)spiro[1,2-dioxetane-3,2'-adamantane], which is detected with a luminometer. Embodiments of horse radish peroxidase substrates include 2,2' azino-bis(3-ethylbenzthiazoline-6 sulfonic acid) (ABTS), 5-aminosalicylic acid (5AS), o-dianisidine, and o-phenylenediamine (OPD), which can be detected with a spectrophotometer; and 3,3,5,5'-tetramethylbenzidine (TMB), 3,3' diaminobenzidine (DAB), 3-amino-9-ethylcarbazole (AEC), and 4-chloro-1-naphthol (4C1N), which can be detected visually. Other suitable substrates are known to those skilled in the art.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Assays

Immunoassays, including radioimmunoassays, enzyme-linked immunoassays and two-antibody sandwich assays as described further below, are useful in the methods of several embodiments provided herein. Furthermore, monoclonal and polyclonal anti-HMGB1 antibodies useful in immunoassays can be readily obtained from a variety of sources as described above. A variety of immunoassay formats, including competitive and non-competitive immunoassay formats, antigen capture assays and two-antibody sandwich assays also are useful the methods of the invention (Self and Cook, Curr. Opin. Biotechnol. 7:60-65 (1996), which is herein incorporated by reference in its entirety). In one embodiment, a method of the invention relies on one or more antigen capture assays. In an antigen capture assay, antibody is bound to a solid phase, and sample is added such that HMGB1 antigen is bound by the antibody. After unbound proteins are removed by washing, the amount of bound antigen can be quantitated, if desired, using, for example, a radioassay (Harlow and Lane, Antibodies A Laboratory Manual Cold Spring Harbor Laboratory: New York, 1988), which is incorporated by reference in its entirety) Immunoassays can be performed under conditions of antibody excess, or as antigen competitions, to quantitate the amount of antigen and, thus, determine a level of HMGB1.

Enzyme-linked immunosorbent assays (ELISAs) can be useful in certain methods of the invention. An enzyme such as horseradish peroxidase (HRP), alkaline phosphatase (AP), β-galactosidase or urease can be linked, for example, to an anti-HMGB1 antibody or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a .beta.-galactosidase detection system can be used with the chromogenic substrate o-nitrophenyl-β-D-galactopyranoside (ONPG) to yield a soluble product detectable at 410 nm, or a urease detection system can be used with a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.) as described further below.

In certain embodiments, HMGB1 can be detected and measured using chemiluminescent detection. For example in certain embodiments, HMGB1 specific antibodies are used to capture HMGB1 present in the biological sample and a antibody specific for the HMGB1 specific antibodies and labeled with an chemiluminescent label is used to detect the HMGB1 present in the sample. Any chemiluminescent label and detection system can be used in the present methods. Chemiluminescent secondary antibodies can be obtained commercially from various sources such as Amersham. Methods of detecting chemiluminescent secondary antibodies are known in the art and are not discussed herein in detail.

Fluorescent detection also can be useful for detecting HMGB1 in certain methods of the invention. Useful fluorochromes include, without limitation, DAPI, fluorescein, Hoechst 33258, R-phycocyanin, B-phycoerythrin, R-phycoerythrin, rhodamine, Texas red and lissamine Fluorescein or rhodamine labeled antibodies, or fluorescein- or rhodamine-labeled secondary antibodies can be useful in the invention.

Radioimmunoassays (RIAs) also can be useful in certain methods of the invention. Such assays are well known in the art. Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of HMGB1 can be performed using a spectrophotometer such as an EMAX Microplate Reader (Molecular Devices; Menlo Park, Calif.) in accordance with the manufacturer's instructions. The assays of the invention can be automated or performed robotically, if desired, and that the signal from multiple samples can be detected simultaneously.

The methods of the invention also encompass the use of capillary electrophoresis based immunoassays (CEIA), which can be automated, if desired. Immunoassays also can be used in conjunction with laser-induced fluorescence as described, for example, in Schmalzing and Nashabeh, Electrophoresis 18:2184-93 (1997), and Bao, J. Chromatogr. B. Biomed. Sci. 699:463-80 (1997), each of which is herein incorporated by reference in its entirety. Liposome immunoassays, such as flow-injection liposome immunoassays and liposome immunosensors, also can be used to detect HMGB1 or to determine a level of HMGB1 according to certain methods of the invention (Rongen et al., J. Immunol. Methods 204:105-133 (1997), which is herein incorporated by reference in its entirety).

Sandwich enzyme immunoassays also can be useful in certain methods of the invention. In a two-antibody sandwich assay, a first antibody is bound to a solid support, and the antigen is allowed to bind to the first antibody. The amount of HMGB1 is quantitated by measuring the amount of a second antibody that binds to it.

Quantitative western blotting also can be used to detect HMGB1 or to determine a level of HMGB1 in a method of the invention. Western blots can be quantitated by well known methods such as scanning densitometry. As an example, protein samples are electrophoresed on 10% SDS-PAGE Laemmli gels. Primary murine monoclonal antibodies, for example, against HMGB1 are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., J. Vasc. Surg. 28:669-675 (1998), which is herein incorporated by reference in its entirety.

As described herein above, immunoassays including, for example, enzyme-linked immunosorbent assays, radioimmunoassays and quantitative western analysis, can be useful in the diagnostic methods of the invention. Such assays typically rely on one or more antibodies. Any of the antibodies described herein may be suitable for use with these immunoassays.

In several embodiments provided herein, methods of diagnosing asbestos exposure or mesothelioma in a subject may include diagnosing the subject as having been exposed to asbestos or having mesothelioma when the level of HMGB1 in the sample is greater than a predetermined level. In various embodiments, the level of HMGB1 in the sample (e.g. serum) and/or the predetermined level can be measured by ELISA. In several embodiments, the subject may be diagnosed as having been exposed to asbestos or having mesothelioma when the level of HMGB1 in the sample (e.g. serum) is greater than a predetermined level of about 0-250 ng/mL, 0-100 ng/mL, between about 0-75 ng/mL, between about 0-50 ng/mL, between about 0-25 ng/mL, or between about 0-10 ng/mL, which can be measured by ELISA for example. The term "about" as used herein when referring to a measurable value such as an amount, is meant to encompass variations of +/−20%, +/−10%, +/−5%, +/−1%, +/−0.5%, or +/−0.1%, or any number in between these percentages, from the specified value. Thus, in some embodiments, the predetermined level can be 0, 1, 2, 3, 4, 5, 6, 7, 8, 9, 10, 11, 12, 13, 14, 15, 16, 17, 18, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 ng/mL. In some embodiments, the predetermined level can be a level that is at least 5% above the level of a comparison subject, for example, a subject that has no disease or exposure or a subject that has a different disease (e.g., lung cancer v. mesothelioma). In some aspects the predetermined level can a level that is at least 5% up to about 100% or up to about 200% or more, greater than the level of the comparison subject, or any value or subrange therebetween.

In several embodiments, the subject can be diagnosed as having been exposed to asbestos or having mesothelioma when the level of HMGB1 in the sample is qualitatively greater than a predetermined level. Any of the detection assays described herein that permit a qualitative comparison between the subject's sample and the predetermined level can be used to diagnose asbestos exposure or presence of mesothelioma.

While the present invention has been described in some detail for purposes of clarity and understanding, one skilled in the art will appreciate that various changes in form and detail can be made without departing from the true scope of the invention.

EXAMPLES

Having generally described embodiments drawn to methods of diagnosing asbestos exposure or mesothelioma, and methods of differentiating whether a tumor of the lung is lung cancer or mesothelioma, a further understanding can be obtained by reference to certain specific examples which are provided herein for purposes of illustration only, and are not intended to be limiting.

Example 1

HMGB1 is Highly Expressed in Mesothelioma but not in Lung Cancer

Figure 2:
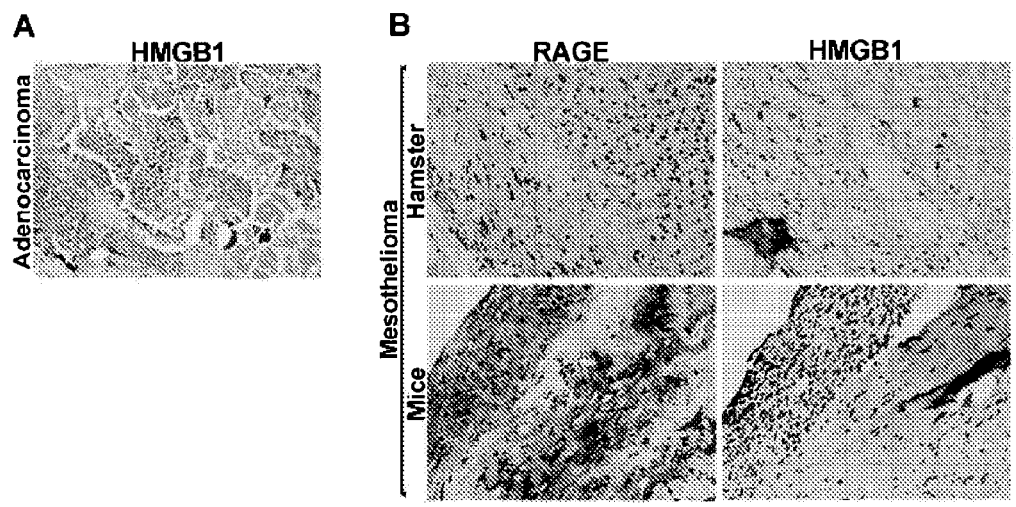
FIGS. 2A and 2B shows HMGB1 and RAGE are upregulated in mesothelioma tumors from MM animal models as detected by immunostaining.

HMGB1 expression was analyzed by immunohistochemistry in 30 MM biopsies and compared to 20 lung cancer biopsies (10 small cell lung cancer (SCC) and 10 non-small cell lung cancer (NSCC)). HMGB1 was detected in both nucleus and cytoplasm in over 90% of tumor cells in 30/30 MM biopsies representing all 3 main histological subtypes of MM (epithelial, biphasic and sarcomatoid) (FIG. 1A). Instead, stromal cells in MM biopsies and tumor and stromal cells in the 20 lung cancer biopsies showed only nuclear staining and did not show cytoplasmic staining (FIG. 1B). The same results were observed in our hamster and mouse MM models: 6/6 mesothelioma induced in hamsters and 10/10 mesothelioma induced in mice by injection of crocidolite asbestos expressed high levels of nuclear and cytoplasmic HMGB1 (FIG. 2).

Briefly, immunostaining analyses were conducted according to standard procedures Immunohistochemistry was performed on human, hamster and mouse tissues with rabbit polyclonal anti-HMGB1 and rabbit polyclonal anti-RAGE (Abcam, Cambridge, Mass.), both diluted 1:200. Matching rabbit IgG isotype were used as controls. Immunocytochemistry was performed using the Vectastain ABC kit (Vector Labs, Burlingame, Calif.) according to the manufacturer's instructions. Mouse monoclonal IgG purified anti-HMGB1 (Abcam) was used in 1:500 dilution for the detection of intracellular HMGB1 protein. Matching mouse IgG were used as control.

The animal experiments for the induction of mesothelioma through asbestos exposure were performed as described (Yang H, et al. Programmed necrosis induced by asbestos in human mesothelial cells causes high-mobility group box 1 protein release and resultant inflammation. Proc Natl Acad Sci USA. 2010; 107(28):12611-12616), which is herein incorporated by reference in its entirety. Briefly, 6 female Syrian hamsters and 10 BALB/c mice that were 21-day-old (to test for interspecies variability) were injected intraperitoneally with 0.4 mg crocidolite in PBS every 2nd week for 10 weeks, for a total amount of 4 mg. Control groups (6 hamsters and 10 mice) were injected with PBS. Animals were killed after 4 months. All of the major organs were evaluated and studied histologically.

Example 2

HMGB1 is Highly Expressed in Sera of Mesothelioma Patients

The high level of expression of HMGB1 by MM tumor cells, and the abnormal presence of HMGB1 in the cytoplasm of these cells, suggested that HMGB1 might be secreted or released into the stroma, making its way into the patient's serum. The levels of HMGB1 in serum samples from 20 MM patients and 20 age- and gender-matched healthy individuals were determined. The serum levels of HMGB1 (mean±SEM) in MM patients were significantly higher (77.9±9.4 ng/ml) than in healthy controls (17.5±3.2 ng/ml: P<0.0001; FIG. 1C). These data show that HMGB1 can be used as a serum biomarker for mesothelioma diagnosis.

The human HMGB1 ELISA kit (IBL International, Germany) was used to measure the levels of HMGB1 in patients' sera and in HM and MM conditioned media. Samples were tested in duplicates. Sera were obtained from 20 untreated mesothelioma patients and 20 age- and gender-matched healthy individuals. All participants provided informed consent, and procedures and protocols were approved by the institutional review board (IRB). For the detection of extracellular HMGB1 released by MM and HM, cells were cultured in DMEM with 1% FBS at 37° C., 5% CO2 for 24 hours. The culture media were then collected and concentrated by ultrafiltration using Amicon Ultra Centrifugal Filters (Millipore, Billerica, Mass.) and 10 µl aliquots were used in duplicates to perform the ELISA assays. Experiments were performed twice.

Example 3

HMGB1 is Highly Expressed in Sera of Subjects Exposed to Asbestos

Figure 3:
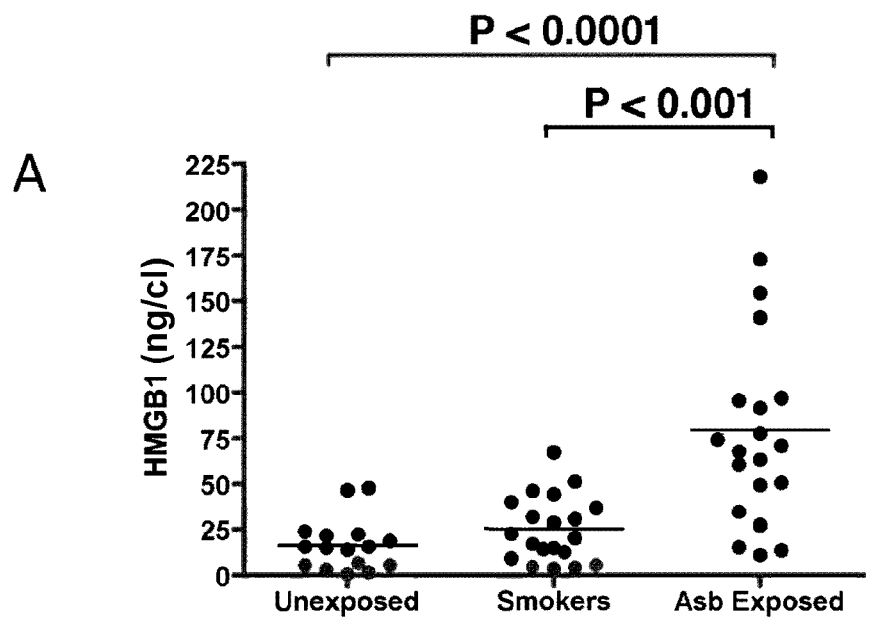
FIGS. 3A and 3B are graphs showing HMGB1 levels in serum from individuals exposed to asbestos, in heavy smokers, and in nonsmoker, non-asbestos-exposed controls measured by ELISA.
Figure 3:
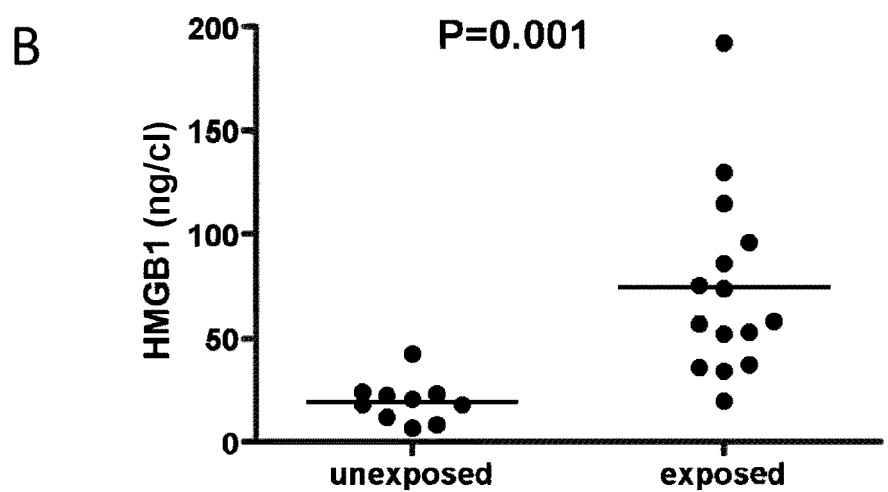

Serum levels of HMGB1 in 20 individuals with a documented history of asbestos exposure were determined (as in Example 2) and compared to 20 heavy smokers with lung inflammation and bronchoscopic evidence of dysplasia but without any history of asbestos exposure, and also with 20 non-smokers, non-asbestos-exposed healthy control individuals. The serum level of HMGB1 (mean±SE) in asbestos-exposed individuals was 80.2±12.4 ng/cl, which was more than four times higher than that observed in non-exposed controls (16.9±3.6 ng/cl, $P<0.0001$) and about three times higher than the levels found in heavy smokers (26.1±4.1 ng/cl) ($P<0.001$) (FIG. 3A). These results were separately reproduced in additional 15 asbestos-exposed individuals compared to non-smokers, healthy controls (FIG. 3B). These results suggest that HMGB1 can be used as a biomarker to identify individuals/cohorts exposed to asbestos.

Example 4

HMGB1 and RAGE are Both Upregulated in MM Cells

Expression levels of HMGB1 and its receptors RAGE, TLR2 and TLR4 in a panel of 8 MM cell lines and 8 distinct primary HM cultures were determined Primary human mesothelial cells (HM) were obtained from pleural effusions of eight different patients, pathologically diagnosed free of malignancy at the Queen's Medical Center, Honolulu, Hi. HM were characterized by calretinin, pancytokeratin, and carcinoembryonic antigen (CEA) immunostaining, as previously described (Bocchetta M, et al., "Human mesothelial cells are unusually susceptible to simian virus 40-mediated transformation and asbestos cocarcinogenicity," Proc Natl Acad Sci USA. 2000; 97:10214-10219). HM were cultured in Dulbecco's Modified Eagle Medium (DMEM) (Mediatech Inc., Manassas, Va.) containing 20% fetal bovine serum (FBS) (Gibco, Carlsbad, Calif.) and penicillin-streptomycin (100 units/ml penicillin G and 100 µg/ml streptomycin sulfate) (GIBCO), and were used between second and fifth passages. THP-1 human monocytes (ATCC, Manassas, Va.) were differentiated into macrophages by phorbol 12-myristate 13-acetate (TPA). The pleural malignant mesothelioma (MM) cell lines were established from surgically resected human MM specimens and used comparatively in our studies. REN cells were provided by Dr. Steven Albelda (University of Pennsylvania, Philadelphia, Pa.), while all other cell lines used in this study were provided by Dr. Harvey I. Pass (NYU School of Medicine, New York, N.Y.). MM cells were maintained in DMEM containing 10% FBS. All cells were cultured at 37° C. in a humidified atmosphere with 5% $CO_2$ and grown to approximately 80-90% confluency. REN/luc luminescent cells were derived from REN cells that were transduced with the lentiviral vector pRRL.sin.PPT.CMV expressing luciferase (53).

Quantitative real-time PCR (qRT-PCR) revealed that in 7 out of 8 MM cell lines the amounts of HMGB1 transcripts were significantly higher compared to HM. Briefly, total RNA from MM and HM cells was isolated using RNeasy kit (Qiagen, Valencia, Calif.) and treated with RNase-free DNase. For each sample, 3 µg of total RNA was reverse transcribed by using the First-Strand cDNA synthesis kit (Fermentas, Canada). β-actin housekeeping gene was used as the internal control for normalization. PCR amplifications for HMGB1, RAGE, TLR2, TLR4 and β-actin were performed in triplicates, by standard procedures, in 25 µl total reaction volumes using the SYBR green master PCR mix (Applied Biosystems, Carlsbad, Calif.) with the GeneAmp 5700 sequence detection system (PerkinElmer-Applied Biosystems). We used the following primers from the QuantiTect Primer Assay method (Qiagen): Hs_AGER_1_SG (QT00000119), Hs_HMGB1_1_SG (QT01002190), Hs_TLR4_2_SG (QT01670123), and Hs_TLR2_1_SG (200) (QT00236131). Amplifications were performed in triplicates and assayed twice. A large degree of variability was observed: PPM-Ada and PPM-Mill cells expressed relatively low levels of HMGB1 transcripts, while in REN and PPM-Phi cells the amount of HMGB1 transcripts exceeded by 6 and 20 times those found in primary HM cells (FIG. 4A).

HMGB1 protein expression and compartmentalization was evaluated by Western blotting by cell fractionation. Briefly, MM and HM cells were lysed and the cytoplasmic and nuclear fractions separated using the protein extraction kit from Active Motif (Carlsbad, Calif.), according to the manufacturer's instructions. Protein concentrations were determined using the BCA method (Thermo Scientific, Fremont, Calif.) and 50 µg of protein lysate from each sample were separated on NuPAGE Novex 4-12% Bis-Tris mini gels (Invitrogen, Carlsbad, Calif.) and transferred to Hybond-C Extra nitrocellulose membranes (Amersham Biosciences, UK). The membranes were blocked in Tris-buffered saline containing 0.05% Tween 20 (TBST) and 5% skim milk at RT for 2 hours; then probed with the primary antibody at 4° C. overnight; mouse monoclonal anti-HMGB1 (1:1000), rabbit polyclonal anti-RAGE (1:1000), mouse monoclonal anti-TLR2 (1:250) and goat polyclonal anti-TLR4 (1:250) were all from Abcam. Anti-α-Tubulin (1:5000; Calbiochem, San Diego, Calif.) and anti-Lamin B (1:1000; Abcam) were used as loading controls for the cytoplasmic and nuclear fractions, respectively. After probing with the primary antibodies, the membranes were washed four times with TBST and incubated with the appropriate horseradish peroxidase-conjugated secondary antibody (Pierce, Rockford, Ill.) at RT for 1 hour. The signal was detected by enhanced chemiluminescence (Pierce). Experiments were performed three times.

Figure 4:
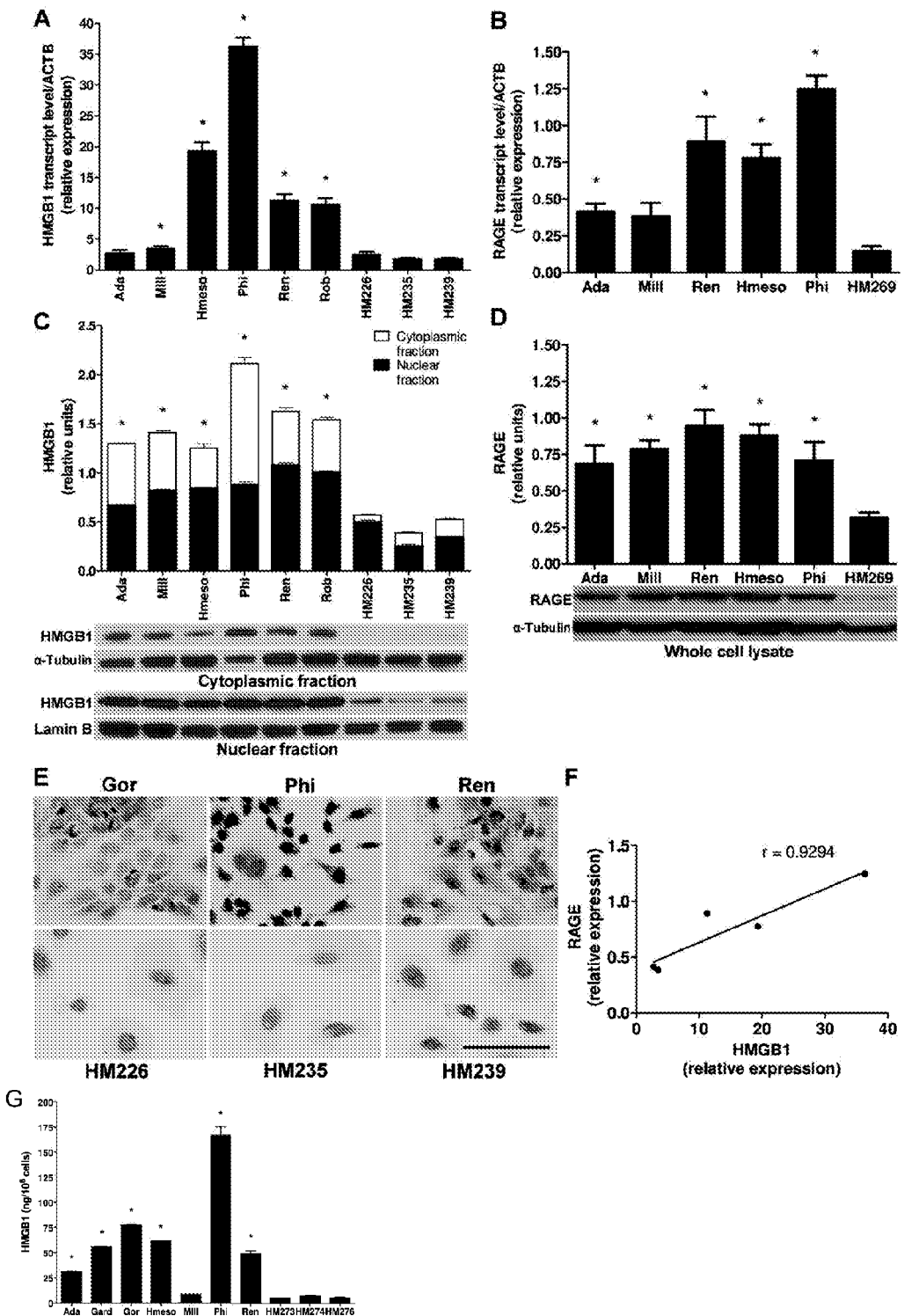
FIG. 4 shows that HMGB1 and RAGE are both upregulated in malignant mesothelioma (MM) cell lines.

In HM, HMGB1 was almost exclusively detected in the nuclear fraction; instead, MM cells contained high amounts of HMGB1 in both the nucleus and the cytoplasm (FIG. 4C). The results were confirmed by immunostaining: MM cells (PPM-Gor, PPM-Phi, and REN) had both nuclear and cytoplasmic HMGB1 staining, while HM cells had exclusively nuclear staining (FIG. 4E).

The amounts of RAGE transcripts paralleled the amounts of HMGB1 mRNA in the MM cell lines (FIG. 4F). Cells with abundant HMGB1 transcripts (PPM-Phi, REN, and PPM-Hmeso) had high amounts of RAGE transcripts, while cells with little HMGB1 mRNA (PPM-Ada and PPM-Mill) had low levels of RAGE mRNA (FIG. 4B). TLR2 and TLR4 transcript expression was also higher in MM than in HM cells, although the overall levels were lower than that of RAGE. The expression levels detected by qRT-PCR were confirmed at the protein level by Western blot analyses (FIG. 4D). In summary, the results indicate that most MM cell lines expressed high levels of HMGB1 and of its main receptors RAGE, TLR2 and TLR4.

Example 5

Asbestos-Induced Human Mesothelial Cell Death Causes HMGB1 Release and is Proinflammatory HMGB1 localization in human mesothelial (HM) cells after asbestos exposure was assessed by immunofluorescence staining. Briefly, HM cells were exposed to crocidolite, $H_2O_2$ (100 μM) or actinomycin D (0.1 μM) for 6 hrs. After fixation and permeabilization, cells were incubated with HMGB1 antibody (BD Bioscience Pharmingen) and a fluorescein-conjugated secondary antibody (Chemicon, Temecula). Nuclei were stained with DAPI.

Figure 5:
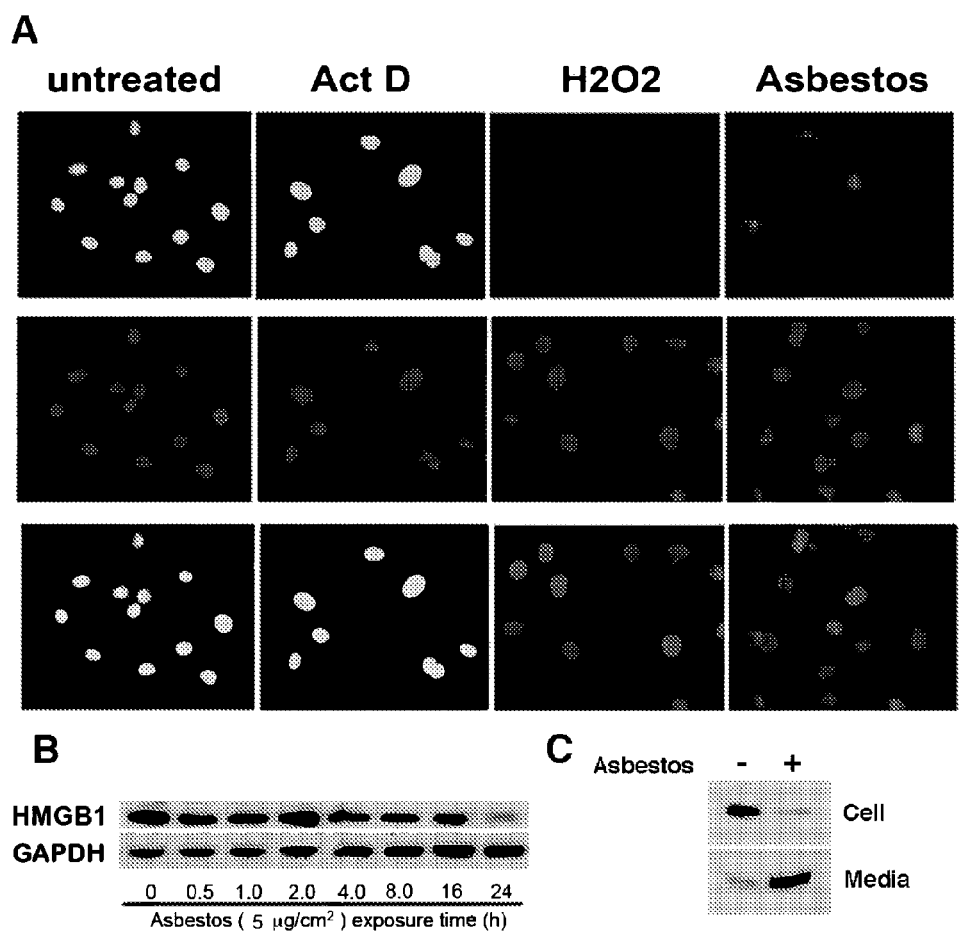
FIG. 5 shows HMGB1 is released from HM into the extracellular space after asbestos exposure.

Six hours after asbestos exposure, HMGB1 translocated from the nucleus into the cytosol, as observed in HM exposed to $H_2O_2$. Conversely, in actinomycin D-exposed HM cells, HMGB1 remained within the nucleus (FIG. 5A). To verify the results, whole-cell extracts and concentrated culture medium were analyzed by Western blot. After 24 hrs of asbestos exposure, HMGB1 was released into the media in concert with cell death (FIGS. 5B and C). Release of HMGB1 into the extra-cellular space was paralleled by an increase in HMGB1 transcripts.

Figure 6:
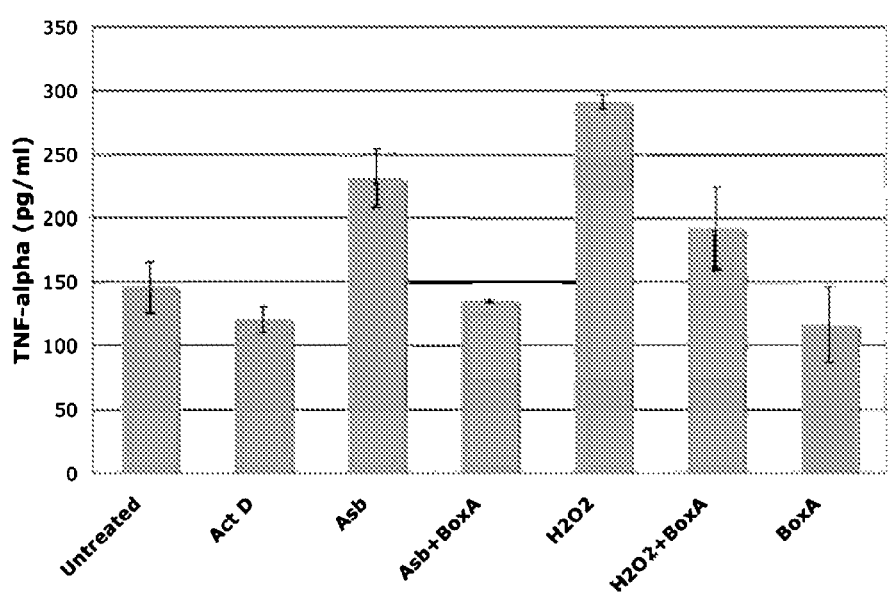
FIG. 6 is a graph that shows asbestos-induced cell death and the release of HMGB1 promote TNF-α secretion by macrophages.

Next, it was determined whether the release of HMGB1 was linked to an inflammatory response. The cell medium was collected, concentrated and added to macrophages in tissue culture. Macrophage activation was measured by the secretion of the pro-inflammatory cytokine TNF-α, which promotes asbestos carcinogenesis. The cell culture medium from asbestos-exposed HM promoted macrophage secretion of TNF-α. Similar results were obtained using the culture medium from HM in which necrosis was induced by $H_2O_2$. The culture medium from HM exposed to actinomycin D (positive control for apoptosis) did not induce TNF-α secretion (FIG. 6). To confirm that the induction of TNF-α secretion by macrophages was mediated through the HMGB1 released by necrotic HM, the culture medium of HM exposed to asbestos was incubated with Box A, a fragment of HMGB1 with antagonist activity. Box A significantly reduced TNF-α secretion by macrophages treated with culture medium from asbestos-exposed HM ($P<0.05$) (FIG. 6). These findings indicated that the release of HMGB1 from asbestos-exposed HM triggers the release of TNF-α and the inflammatory response associated with asbestos carcinogenesis.

Example 6

HMGB1 is Linked to Pathogenesis of Asbestos-Related Disease

The involvement of HMGB1 in the pathogenesis of asbestos-related disease in mouse and hamster asbestos experimental models was addressed. Briefly, six 21-day-old, female Syrian hamsters and 10 Balb/c mice (to test for inter-species variability) were injected intraperitoneally with 0.4 mg crocidolite in PBS every 2 weeks for 10 weeks, for a total amount of 4 mg. Control groups (6 hamsters and 10 mice) were injected with PBS. Animals were euthanized after 4 months. All the major organs were evaluated and studied histologically Immunohistochemical analyses of hamster and mouse tissues were performed as in Example 1.

Figure 7:
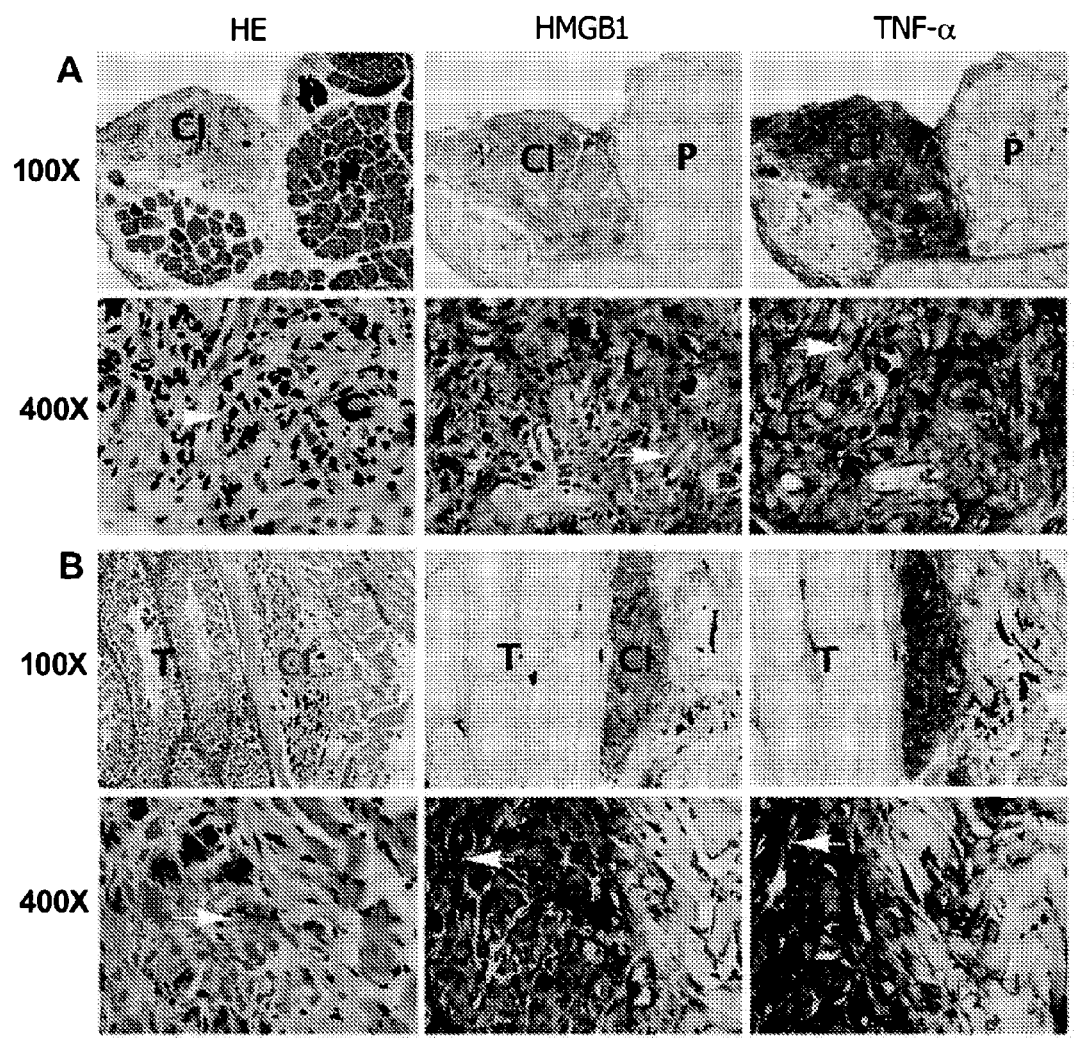
FIGS. 7A and 7B are immunohistochemical images showing strong HMGB1 and TNF-α staining around areas of asbestos deposits in two representative murine specimens.

Chronic inflammation and mesothelial hyperplasia were detected in the peritoneum and tunica vaginalis of all of the injected hamster and mice around areas of asbestos deposits. Histology showed that in these areas, the asbestos fibers were associated with cells with morphology consistent with macrophages, some of them multinucleated (foreign body type histiocytic cells). Several of these cells contained asbestos fibers or part of these fibers in their cytoplasm (phagocytosis). We observed the same phagocytic response when HM or macrophages were grown in tissue culture in the presence of asbestos. Unlike other cell types, such as fibroblasts, we observed that both HM and macrophages phagocytize asbestos Immunohistochemistry (performed on mouse tissues) showed that most of the mononuclear and the multinucleated cells found around asbestos deposits were positive for the macrophage marker, F4/80. In addition, there were scattered lymphocytes (CD4+ and CD8−), plasma cells and HM (pan-cytokeratin+). The inflammatory reaction formed irregular nodules around asbestos deposits. These nodules were situated in the loose connective tissue below the mesothelial covering. The mesothelial cells above these nodules showed focal hyperplasia. HMGB1 and TNF-α staining were specifically localized in these areas. Representative staining of mice specimens are shown in FIG. 7. HMGB1 was localized in both the nuclei and in the cytoplasm of reactive mesothelial and inflammatory cells and in the nearby extra-cellular space, consistent with HMGB1 release from cells undergoing necrosis. Away from areas of asbestos deposits, no chronic inflammation or HMGB1 cytoplasmic staining was detected (FIGS. 7A and B middle panel). These findings were very specific and consistently observed in all the specimens from each of the animals, irrespective of the species. TNF-α expression was detected in the same areas (FIGS. 7A and B right panel), consistent with our in vitro data showing that HMGB1 release leads to TNF-α secretion by inflammatory cells (FIG. 6).

What is claimed is:

1. A method of diagnosing asbestos exposure in a human subject, the method comprising:
   contacting a sample of the human subject with a high-affinity monoclonal antibody specific for HMGB1, wherein the human subject is suspected of prior occupational or environmental asbestos exposure;
   determining whether the amount of the sample bound by the antibody specific for HMGB1 is greater than a predetermined level of at least 3 ng/ml; and
   diagnosing the human subject as having been exposed to asbestos when the amount of the sample bound by the antibody is greater than the predetermined level.

2. A method of differentiating whether a tumor of the lung of a human is lung cancer or mesothelioma comprising:
   contacting at least a portion of a human lung tumor sample with a high-affinity antibody specific for HMGB1;
   determining whether HMGB1 in the portion of the tumor sample is detectable in the nuclei but not the cytoplasm of cells of the tumor sample, or is detectable in both the nuclei and the cytoplasm of cells of the tumor sample; and
   differentiating whether the tumor is lung cancer or mesothelioma based on the detection of HMGB1 in the tumor sample, wherein the tumor is identified as mesothelioma when the HMGB1 is present in the nuclei and cytoplasm.

3. The method of claim 2, wherein the lung cancer is small cell lung cancer.

4. The method of claim 2, wherein the lung cancer is non-small cell lung cancer.

5. The method of claim 2, wherein the lung cancer is lung adenocarcinoma.

6. The method of claim 2, wherein the at least a portion of the tumor sample is a biopsy from a subject.

7. The method of claim 2, wherein HMGB1 in the tumor sample is detected by immunohistochemistry.

8. The method of claim 1, wherein the predetermined level comprises 5 ng/mL.

9. The method of claim 1, wherein the predetermined level comprises 7 ng/mL.

10. The method of claim 1, wherein the amount of HMGB1 in the sample bound by the antibody is determined by ELISA.

11. The method of claim 1, wherein the amount of HMGB1 in the sample bound by the antibody is determined by quantitative western blotting.

* * * * *